United States Patent [19]

Green

[11] Patent Number: 4,556,058

[45] Date of Patent: Dec. 3, 1985

[54] APPARATUS FOR LIGATION AND DIVISION WITH FIXED JAWS

[75] Inventor: David T. Green, Norwalk, Conn.

[73] Assignee: United States Surgical Corporation, Norwalk, Conn.

[21] Appl. No.: 570,213

[22] Filed: Jan. 12, 1984

Related U.S. Application Data

[63] Continuation-in-part of Ser. No. 524,078, Aug. 17, 1983, abandoned, which is a continuation-in-part of Ser. No. 480,436, Mar. 30, 1983, abandoned.

[51] Int. Cl.[4] ............................................. A61B 17/12
[52] U.S. Cl. .................................... 128/305; 128/325; 128/326; 128/334 R; 128/346; 227/DIG. 1; 29/243.56
[58] Field of Search .................... 128/305, 334 R, 325, 128/326; 227/DIG. 1 B, DIG. 1 C; 72/410; 29/243.56

[56] References Cited

U.S. PATENT DOCUMENTS

| | | | |
|---|---|---|---|
| 3,006,344 | 10/1961 | Vogelfanger | 128/318 |
| 3,079,608 | 3/1963 | Babkin | 1/187 |
| 3,175,556 | 3/1965 | Wood et al. | 128/305 |
| 3,363,628 | 1/1968 | Wood | 227/DIG. 1 C |
| 3,545,444 | 12/1970 | Green | 128/305 |
| 3,584,628 | 6/1971 | Green | 128/305 |
| 3,665,924 | 5/1972 | Noiles et al. | 128/305 |
| 3,675,688 | 7/1972 | Bryan et al. | 140/93 D |
| 3,683,927 | 8/1972 | Noiles | 128/334 R |
| 3,735,762 | 5/1973 | Bryan et al. | 128/305 |
| 3,740,994 | 6/1973 | DeCarlo, Jr. | 72/407 |
| 3,775,825 | 12/1978 | Wood et al. | 29/212 D |
| 3,889,683 | 6/1975 | Kapitanov et al. | 128/305 |
| 3,955,581 | 5/1976 | Spasiano et al. | 128/334 R |
| 4,026,294 | 5/1977 | Mattler | 128/305 |
| 4,086,926 | 5/1978 | Green et al. | 128/334 R |
| 4,182,015 | 1/1980 | Niedecker | 29/243.56 |
| 4,188,953 | 2/1980 | Klieman et al. | 128/325 |
| 4,201,314 | 5/1980 | Samuels et al. | 227/DIG. 1 |
| 4,317,451 | 3/1982 | Cerwin et al. | 227/DIG. 1 |
| 4,349,028 | 9/1982 | Green | 128/305 |
| 4,414,721 | 11/1983 | Hufnagel | 128/325 |
| 4,418,694 | 12/1983 | Beroff et al. | 128/325 |
| 4,425,915 | 1/1984 | Ivanov | 128/325 |
| 4,430,997 | 2/1984 | DiGiovanni et al. | 128/325 |
| 4,476,616 | 10/1984 | Jensen | 29/243.56 |
| 4,492,232 | 1/1985 | Green | 227/DIG. 1 |
| 4,512,345 | 4/1985 | Green | 227/DIG. 1 |

*Primary Examiner*—John Doll
*Assistant Examiner*—Lance Johnson
*Attorney, Agent, or Firm*—Robert R. Jackson; John E. Nathan

[57] ABSTRACT

A surgical instrument for ligating and dividing a tubular vessel. The instrument has two spaced apart channels, each containing surgical ligatures of plastic or plastic-like material. A pusher mechanism associated with each of the channels advances the ligatures along the channels. A cutting mechanism intermediate the two channels is used to divide the tubular vessel. An actuating mechanism is connected to the pusher mechanism and to the cutting mechanism for initiating operation thereof. A sub-housing is associated with each of the channels and is movable with respect to the ligatures and with respect to the cutting mechanism. Ligatures are placed at two spaced apart positions of the tubular vessel to effect ligation. The vessel is divided intermediate the spaced apart ligatures while the vessel is advanced so as to facilitate ejection of the ligatures and prevent stretching of the tissue.

25 Claims, 31 Drawing Figures

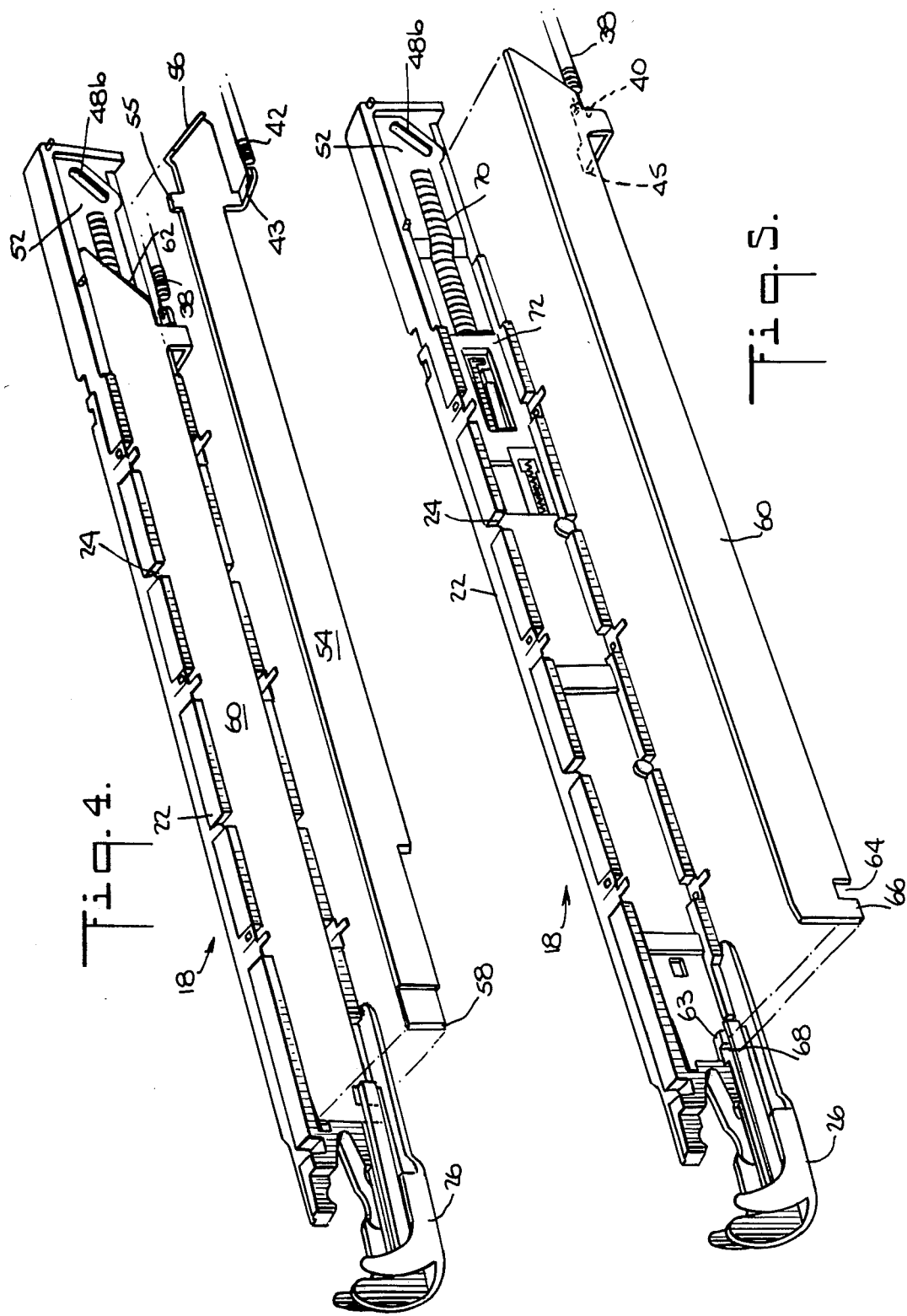

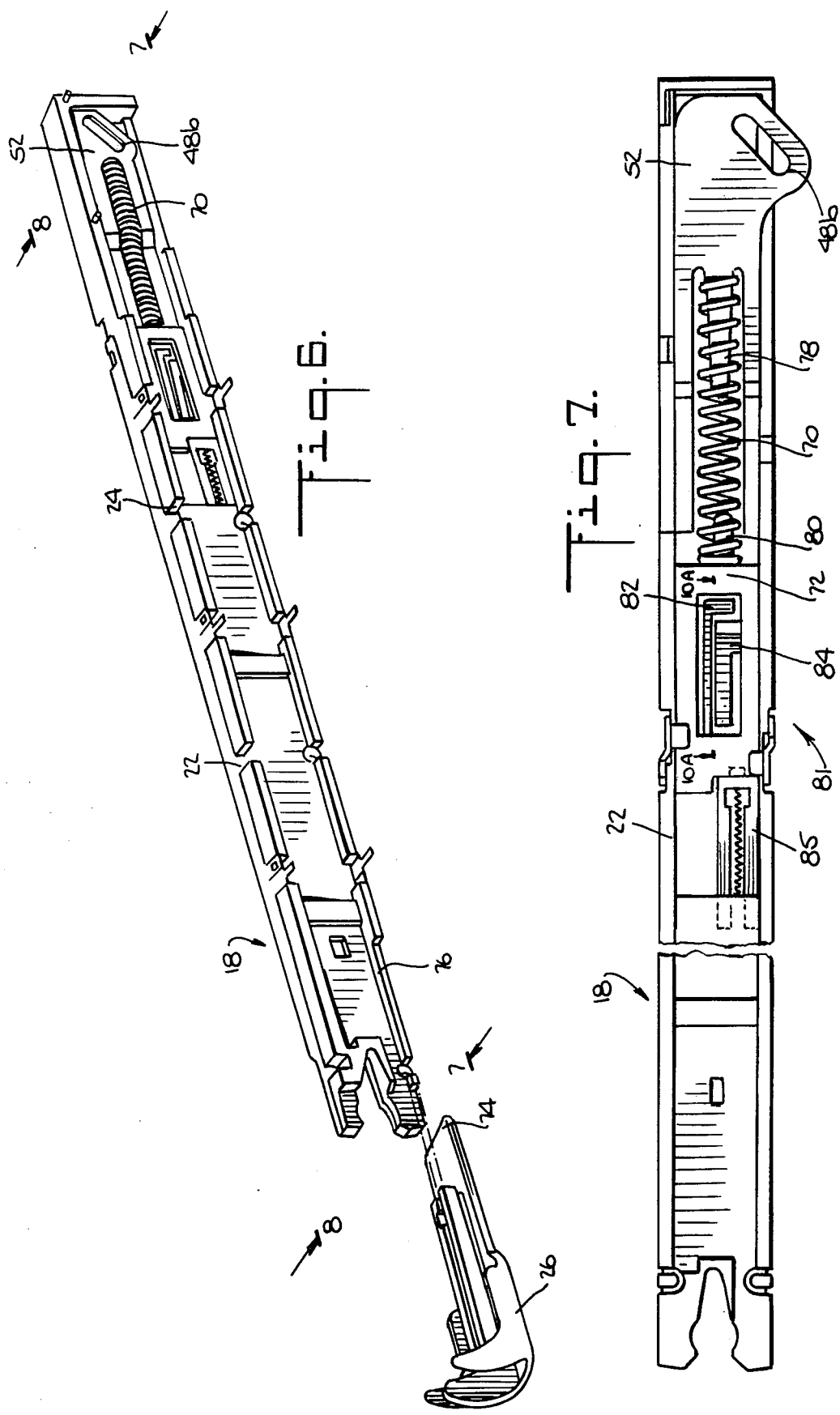

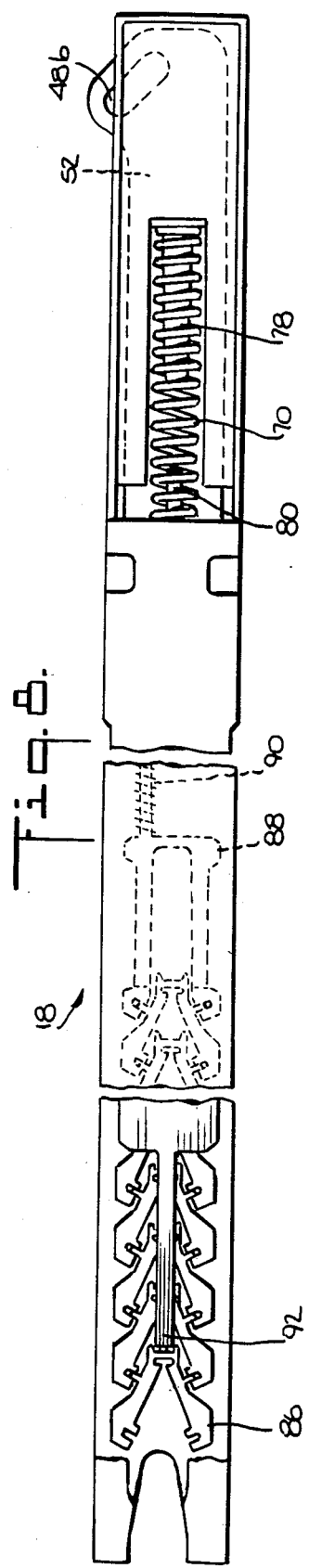
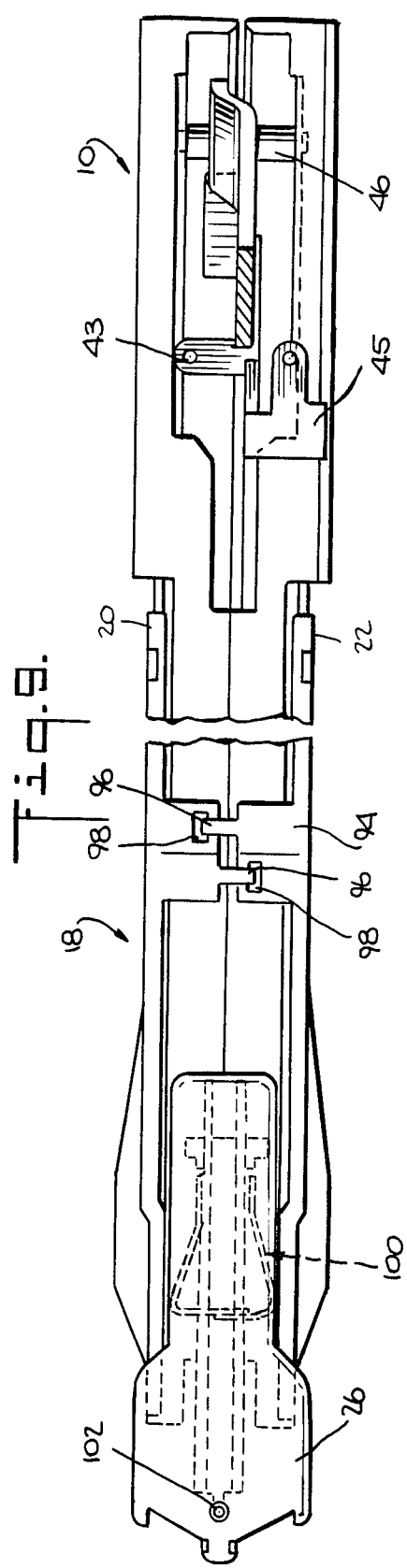

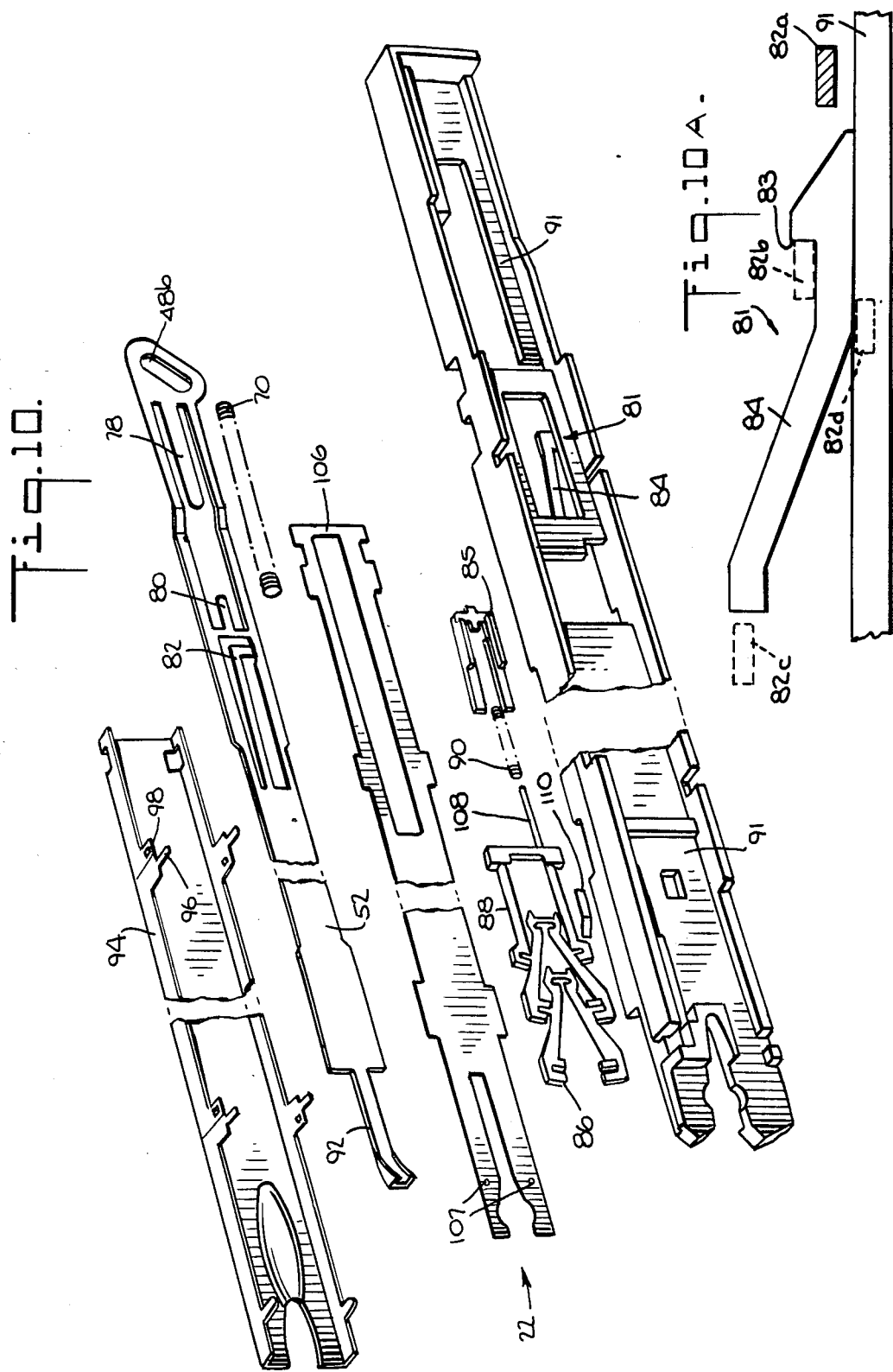

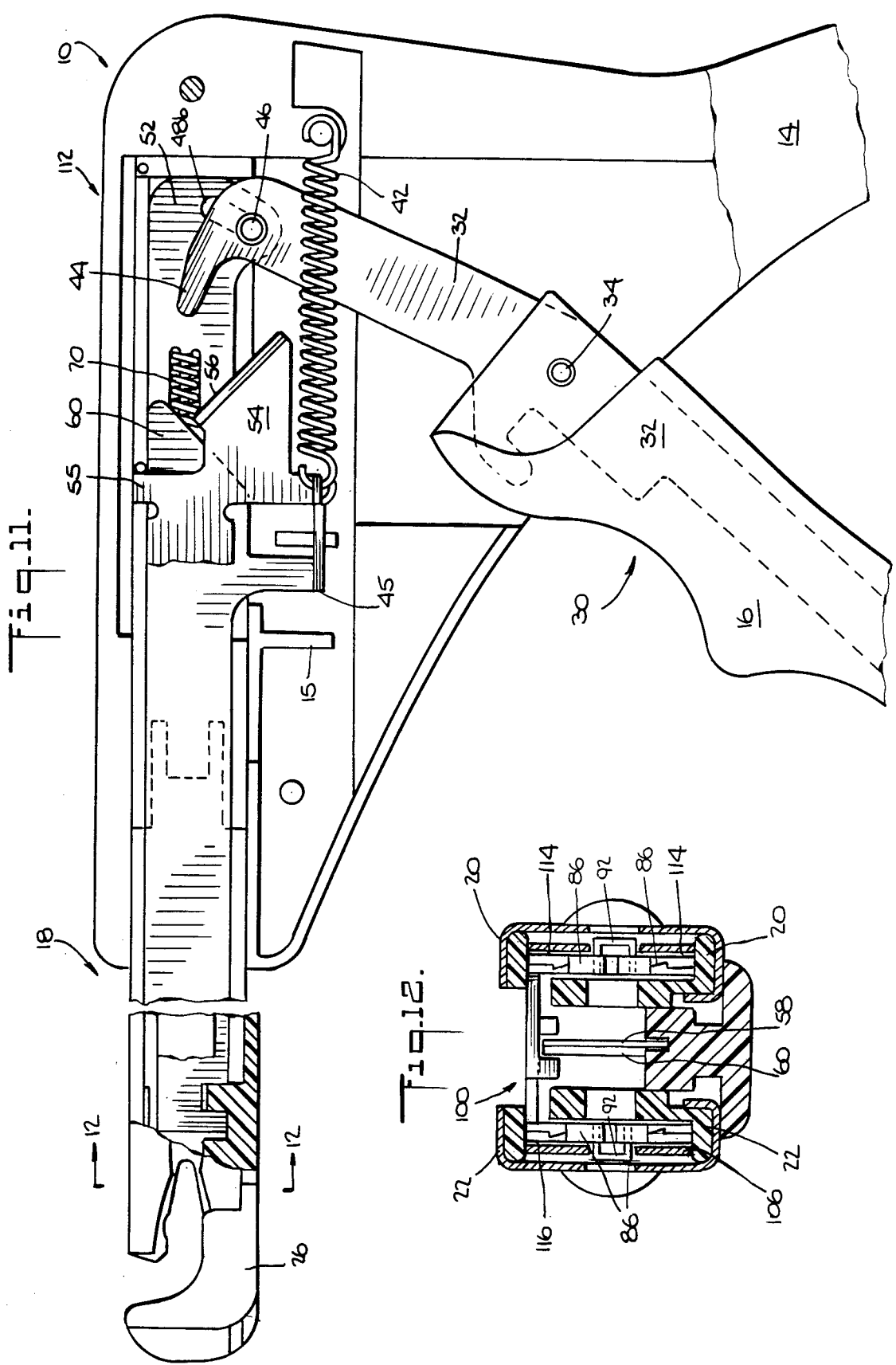

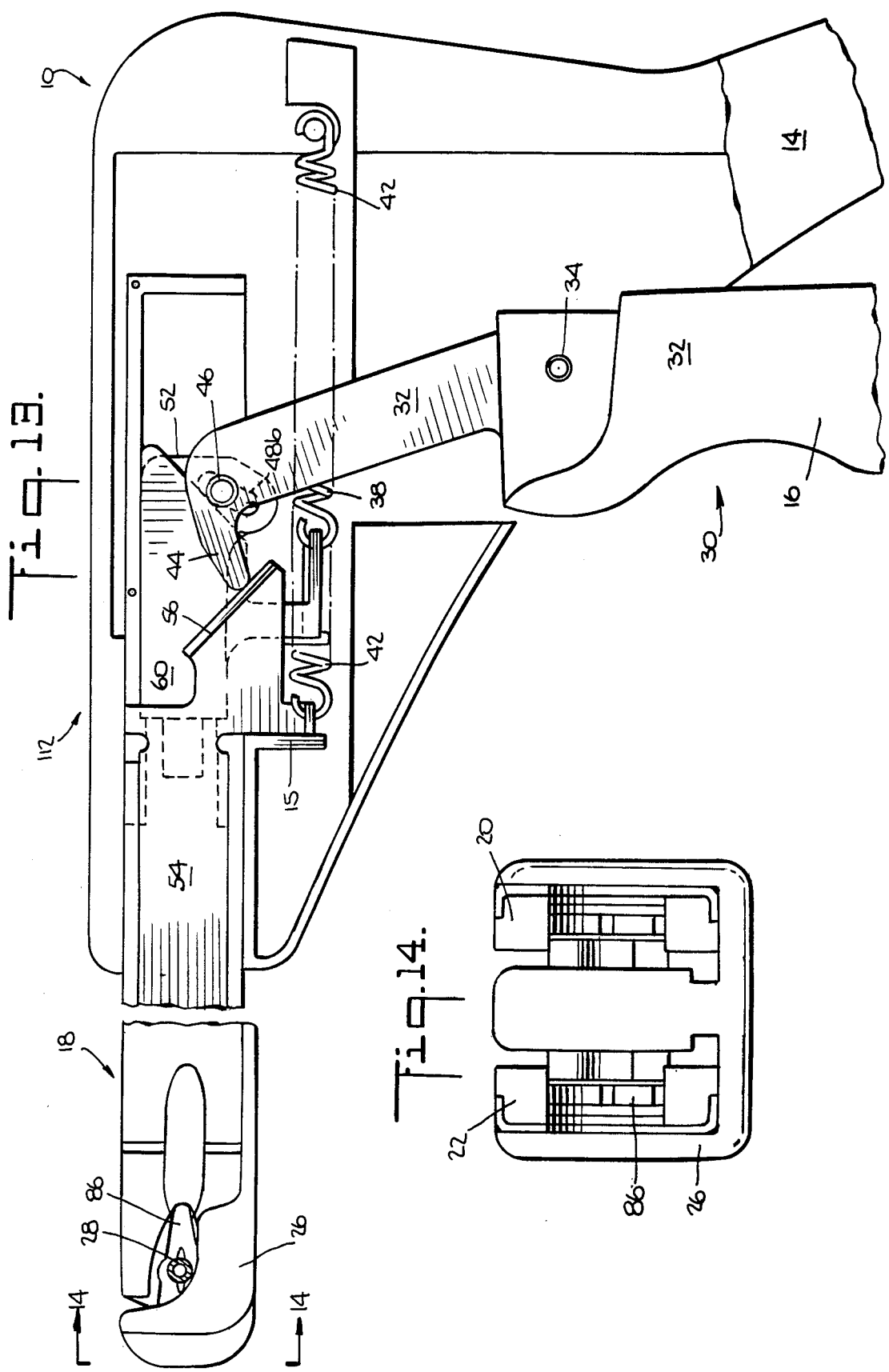

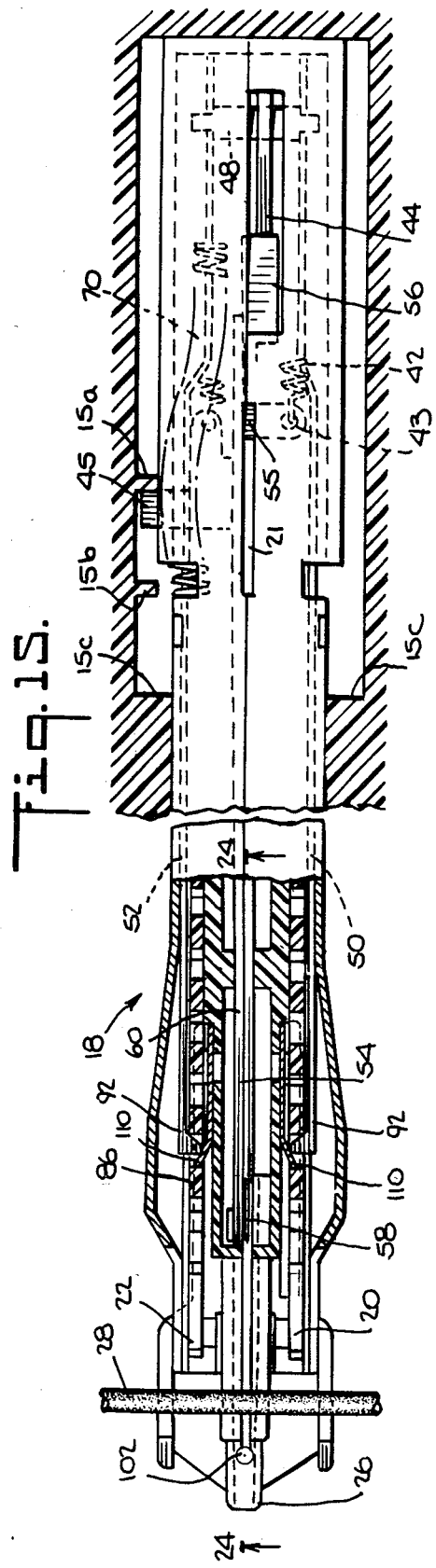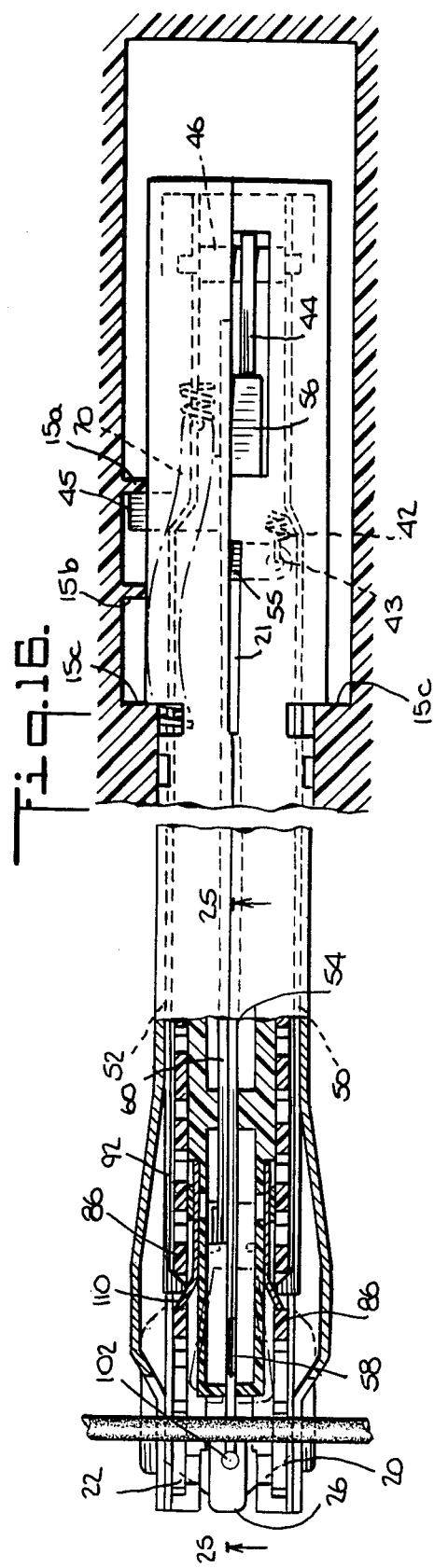

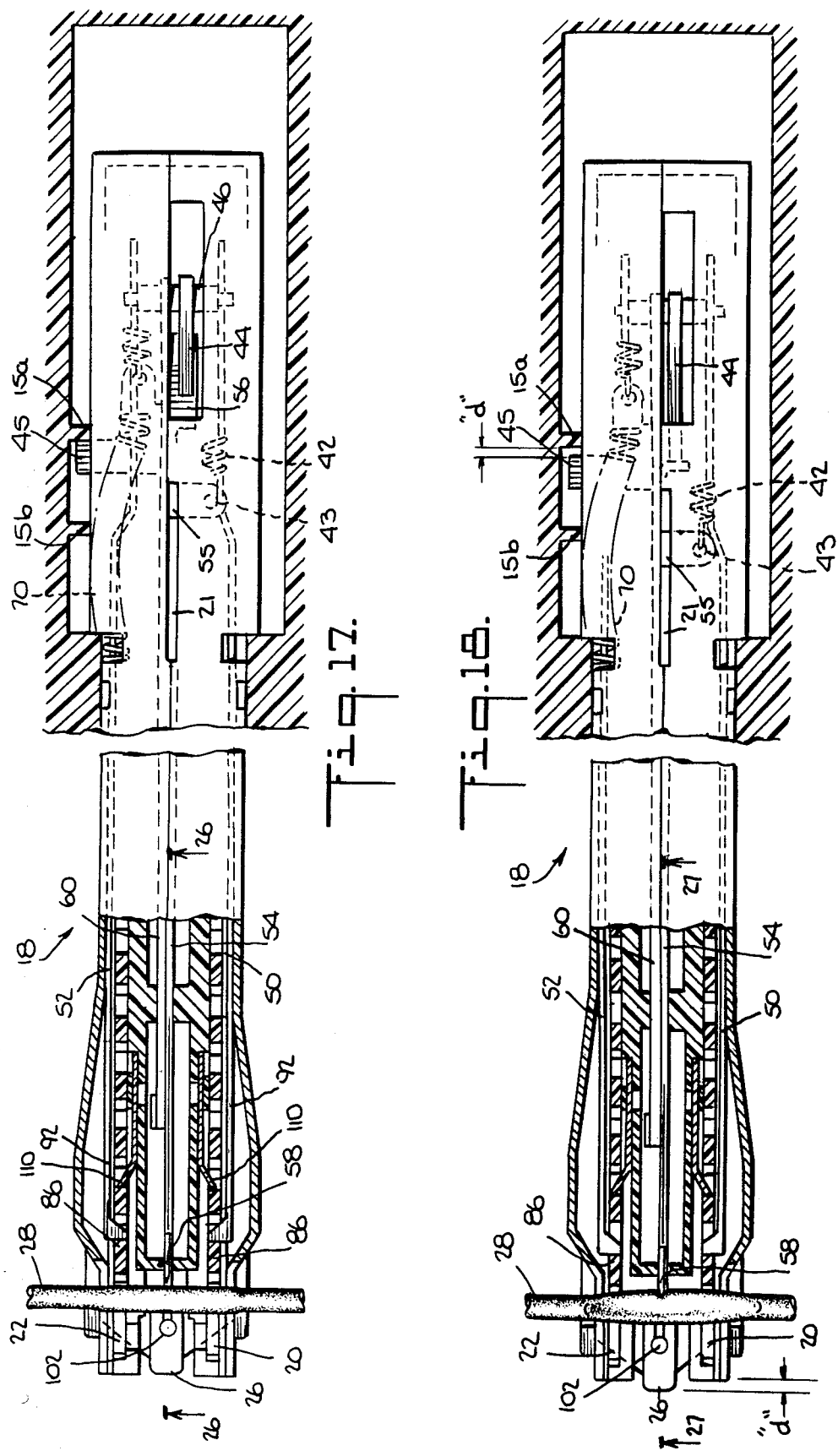

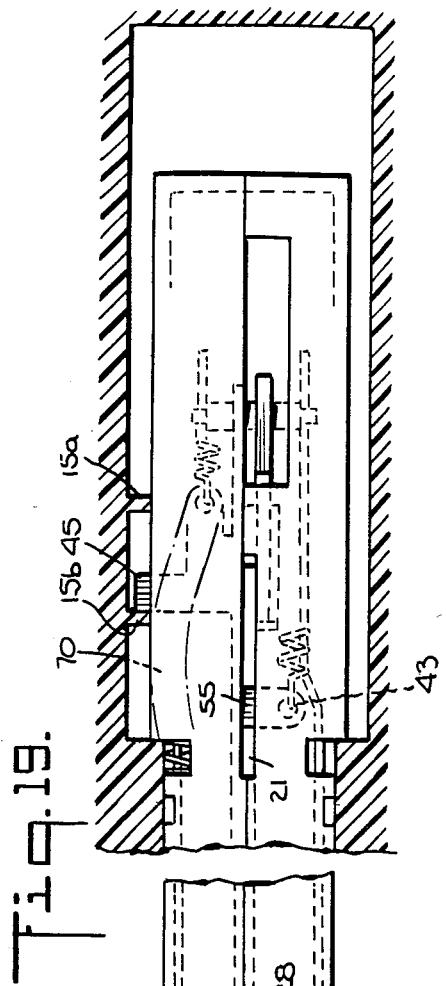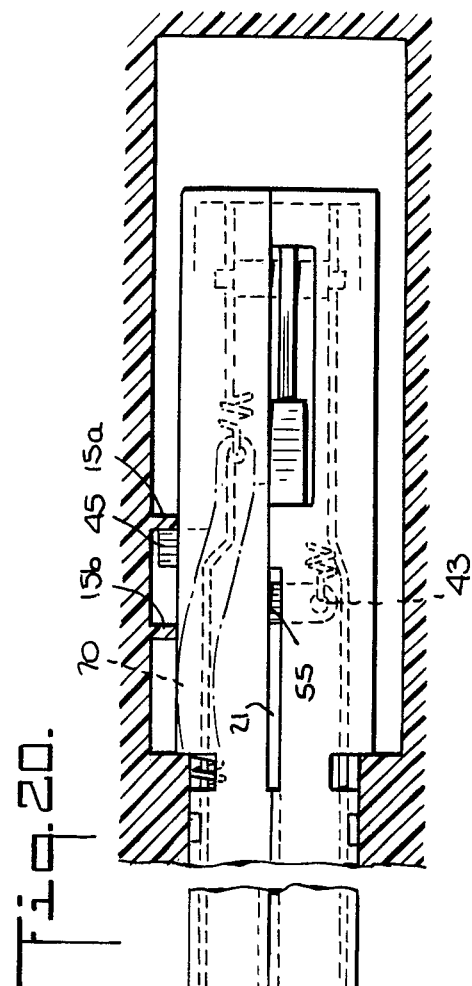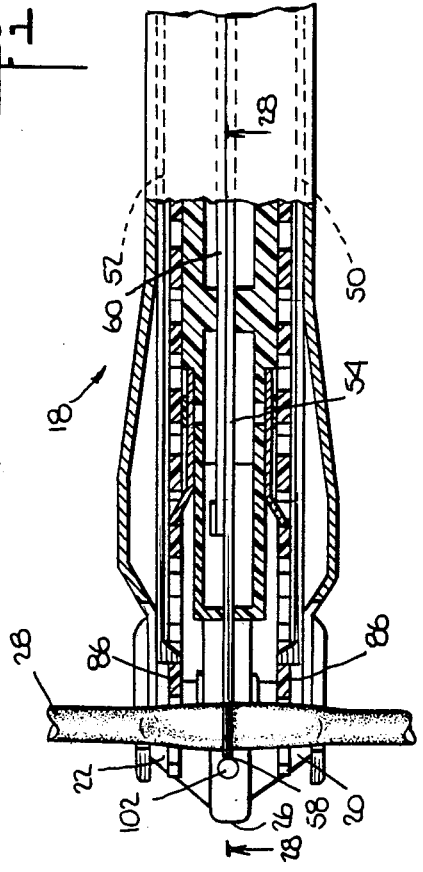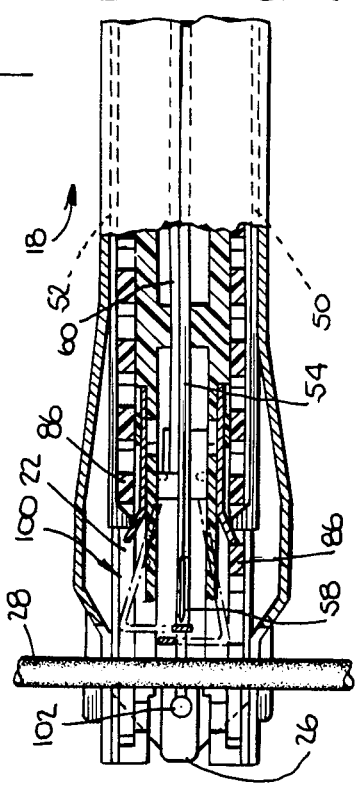
Fig.19.
Fig.20.

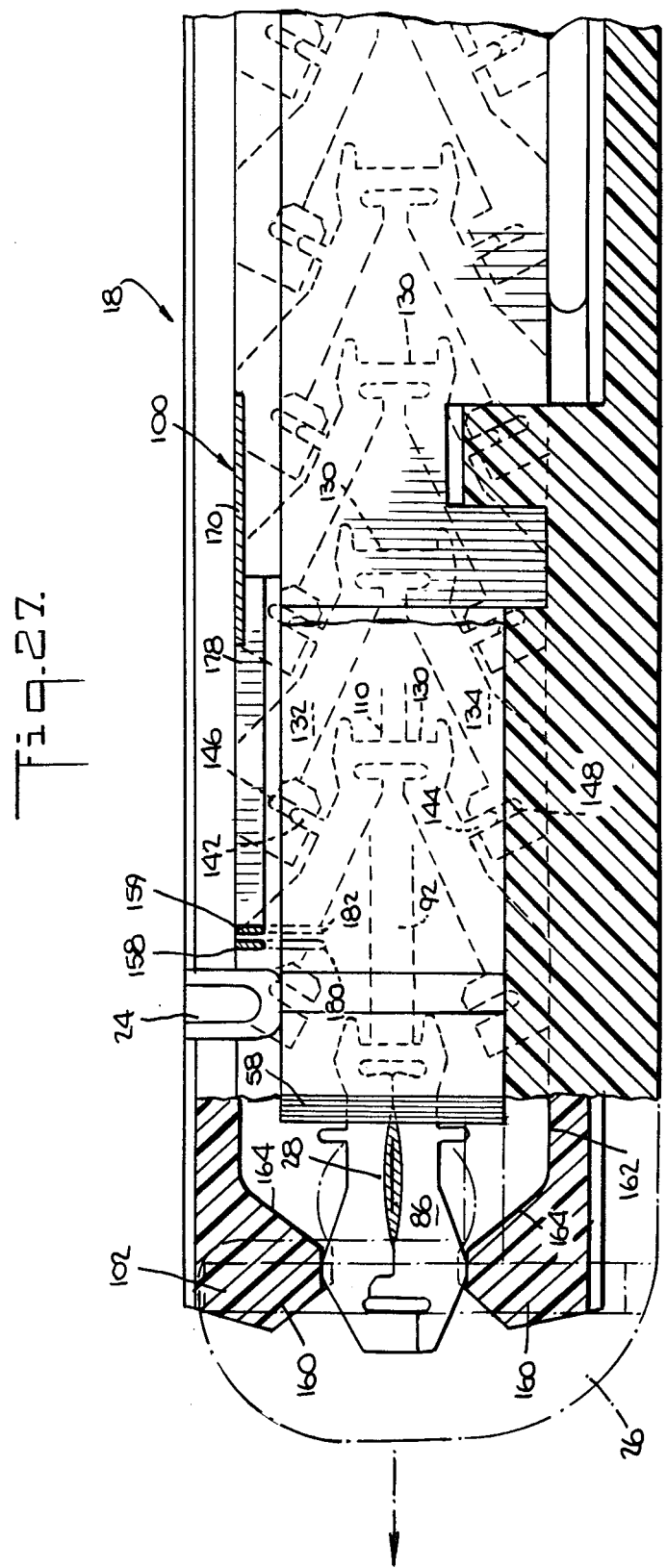

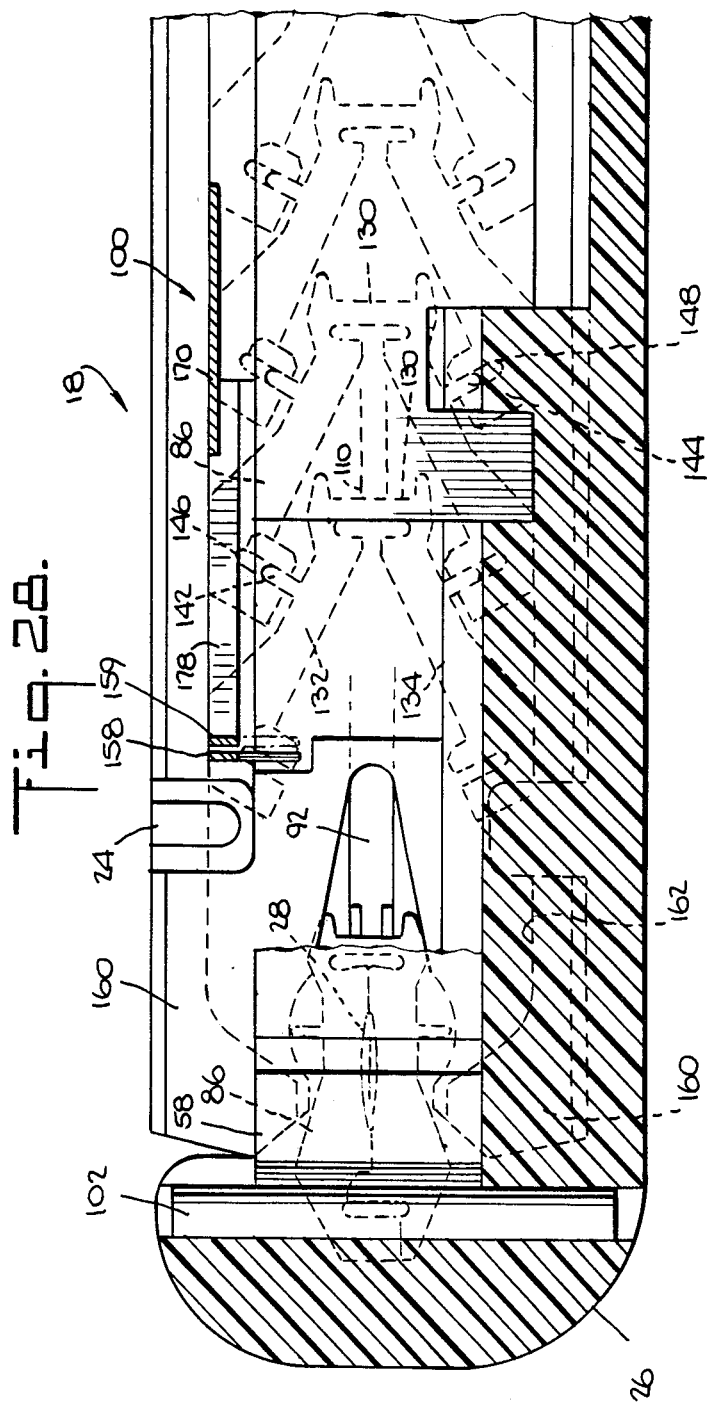

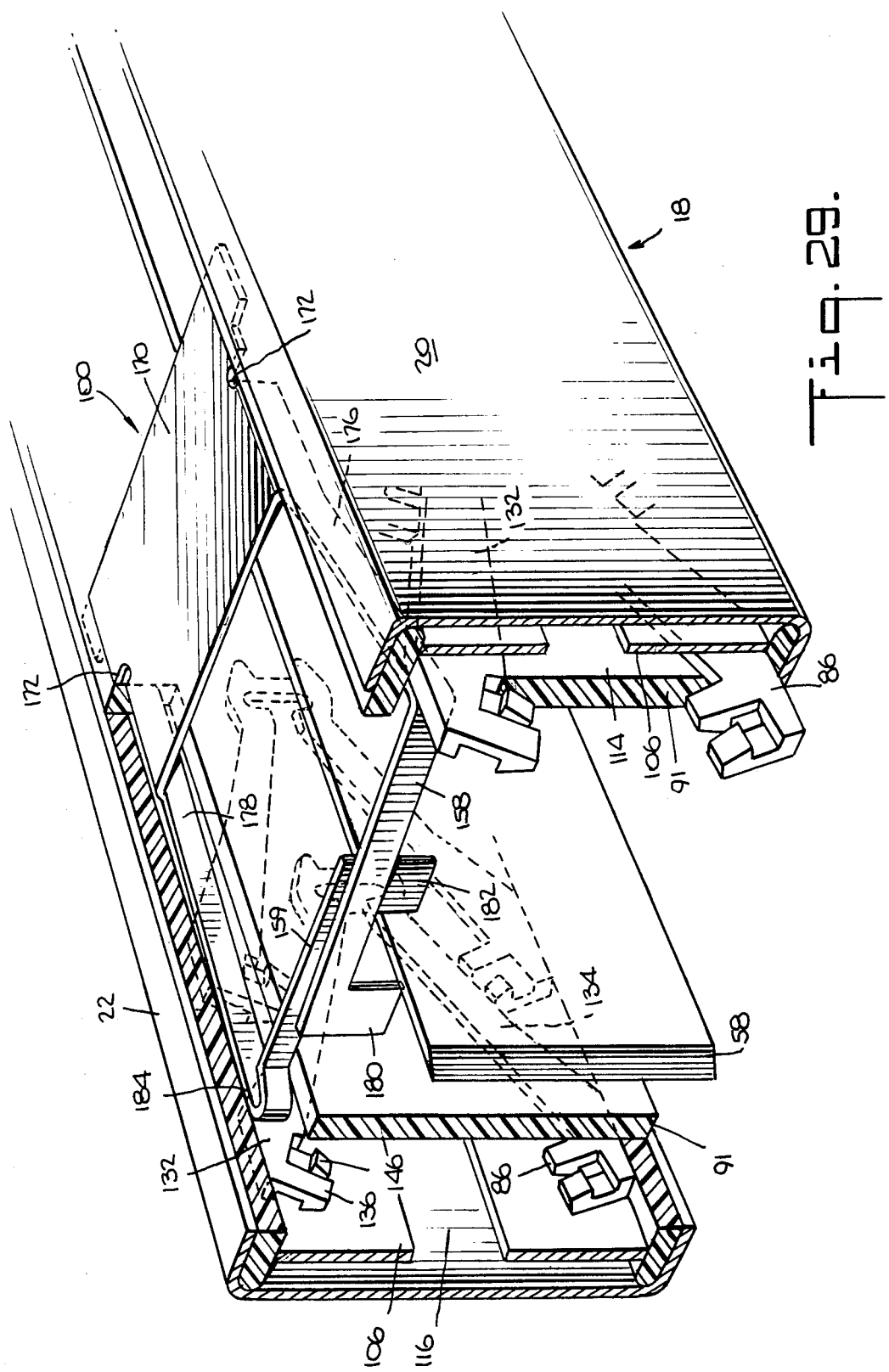

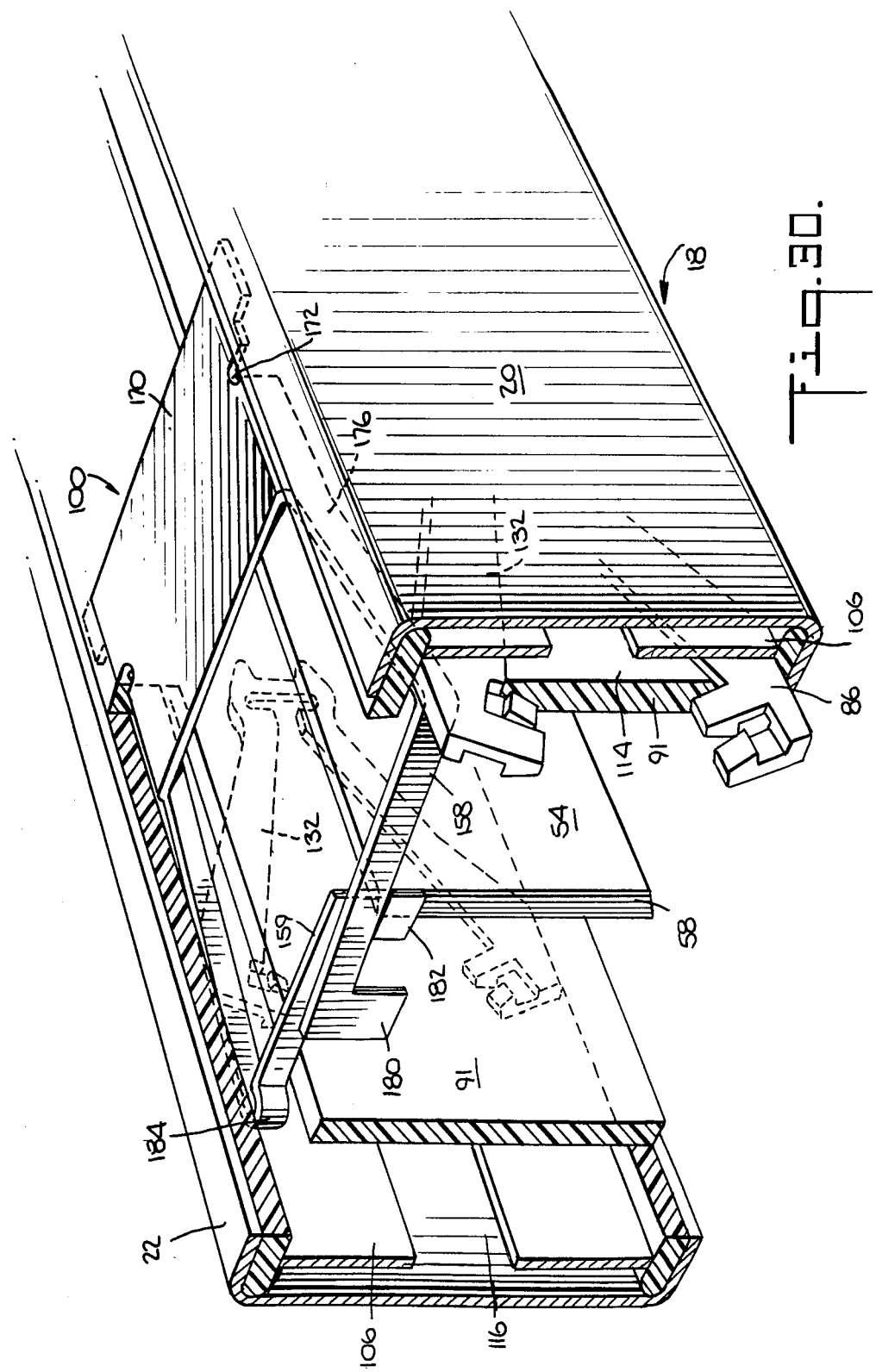

APPARATUS FOR LIGATION AND DIVISION WITH FIXED JAWS

This application is a continuation-in-part of U.S. patent application Ser. No. 524,078, filed Aug. 17, 1983 now abandoned, which is a continuation-in-part of U.S. patent application Ser. No. 480,436, filed Mar. 30, 1983 now abandoned.

BACKGROUND OF THE INVENTION

This invention relates to surgical apparatus, and more particularly to surgical apparatus used to occlude or ligate and to divide body tissue.

Ligating and dividing surgical instruments have typically used metal staples, fasteners, or ligatures to ligate organic tissue structures such as blood vessels. One such system is disclosed in Spasiano et al. U.S. Pat. No. 3,955,581. The apparatus described in that patent operates in three stages to positively control the operations of its metal staple-carrying cartridge. The main body of the cartridge is moved forward toward an anvil assembly fixed on the instrument, thereby enclosing the tissue structure within the jaws of the cartridge. A pair of metal staples is then pushed forward to encircle the tissue structure at spaced apart locations. The staples are crimped or clinched against the fixed anvil assembly to ligate the tissue at the locations of the staples. Finally, a knife blade advances to the fixed anvil assembly and divides the tissue structure intermediate the two staples.

Green et al. U.S. Pat. No. 4,086,926 describes another metal staple-carrying cartridge which operates in three stages. Two laterally spaced metal staples are formed around a tissue structure by means of a fixed anvil assembly, thus ligating the tissue structure. A knife then advances to the fixed anvil assembly and divides the ligated structure between the staples. The staple feeding arrangement in that apparatus comprises a pair of belts, each carrying a plurality of staples.

Another ligating and dividing instrument using metal staples as ligatures and a fixed anvil assembly against which the staples are formed is shown in Green U.S. Pat. No. 4,349,028.

For certain surgical procedures, ligatures in the form of fasteners or clips of X-ray-transparent plastic or plastic-like materials may be preferable to X-ray-opaque metal staples. For convenience herein, all such plastic or plastic-like materials will be referred to generically as plastic-like materials. In addition to X-ray transparency, clips of plastic-like material also have the advantage that they can be made biologically absorbable.

Clips of plastic-like material cannot be simply substituted for metal staples in prior ligating and dividing instruments because plastic-like clips cannot be closed by clinching or crimping in the way that metal staples are clinched or crimped. Unlike metal staples, plastic-like clips will not hold a shape to which they are deformed unless parts of the clip mechanically interlock with one another. Thus the means employed in prior ligating and dividing instruments for clinching or crimping metal staples around the tissue are not suitable for use with plastic-like clips. The problems of storing and feeding plastic-like clips are also different from those associated with metal staples.

It is therefore an object of this invention to provide apparatus for ligating and dividing tissue structures which makes use of fasteners or clips of plastic-like material.

SUMMARY OF THE INVENTION

In accordance with the present invention, there is provided a surgical instrument for ligating and dividing organic tissue structures. The instrument has two spaced apart channels, each containing ligatures of plastic-like material. A pusher mechanism associated with each of the channels advances the ligatures along the channels. A cutting mechanism is intermediate the two channels and is used to divide the tubular vessel. An actuating mechanism is connected to the pusher mechanism, and to the cutting mechanism for initiating operation thereof. A sub-housing for restraining the tissue is associated with each of the channels and is movable with respect to the ligatures and with respect to the cutting mechanism. The instrument applies ligatures at two spaced apart positions of the tissue to effect ligation. As the ligatures are closing on the tissue, they are ejected from the channels. The tissue-restraining sub-assembly moves away from the channels to facilitate ejection of the ligatures while still maintaining control of the tissue. At substantially the same time, the cutting mechanism cuts the tissue intermediate the spaced apart ligatures by advancing to the tissue-restraining sub-housing.

BRIEF DESCRIPTION OF THE DRAWING

The aforementioned and other objects and advantages of the invention will be more easily understood and become more apparent with reference to the following detailed description of the invention and the accompanying drawing, in which:

FIG. 4 is an exploded perspective view of the right track and knife assembly of the instrument of FIGS. 1-3;

FIG. 5 is an exploded perspective view of the right track and anvil bar assembly of the instrument of FIGS. 1-4;

FIG. 6 is an exploded perspective view of the right track and anvil assembly of the instrument of FIGS. 1-5;

FIG. 7 is a view taken along the line 7—7 in FIG. 6;

FIG. 8 is a view taken along the line 8—8 in FIG. 6;

FIG. 9 is a bottom view of the clip storage assembly of the instrument of FIGS. 1-8;

FIG. 10 is an exploded perspective view of the right track assembly of the instrument of FIGS. 1-9;

FIG. 10a is a detail view taken along the line 10a—10a in FIG. 7;

FIG. 11 is a sectional side view of the actuating assembly of the instrument of FIGS. 1-10 before a cycle of instrument operation is initiated;

FIG. 12 is a sectional view taken along the line 12—12 in FIG. 11;

FIG. 13 is view similar to FIG. 11 showing the instrument when the trigger has been fully actuated;

FIG. 14 is a view taken along the line 14—14 in FIG. 13;

FIGS. 15-19 are partly sectional top views of the instrument in accordance with the present invention showing five successive stages in the operation of the instrument;

FIG. 20 is a view similar to FIGS. 15–19 showing the safety mechanism with a surgical clip mis-feed;

FIGS. 24–28 are sectional views respectively taken along the lines 24—24, 25—25, 26—26, 27—27, and 28—28 in FIGS. 15–19;

FIG. 29 is a cut-away perspective view of the distal end of the clip storage assembly of the instrument of the present invention showing normal safety operation; and FIG. 30 is a view similar to FIG. 29 showing safety operation during mis-feed.

DETAILED DESCRIPTION OF THE PREFERRED EMBODIMENT

Figure 1:
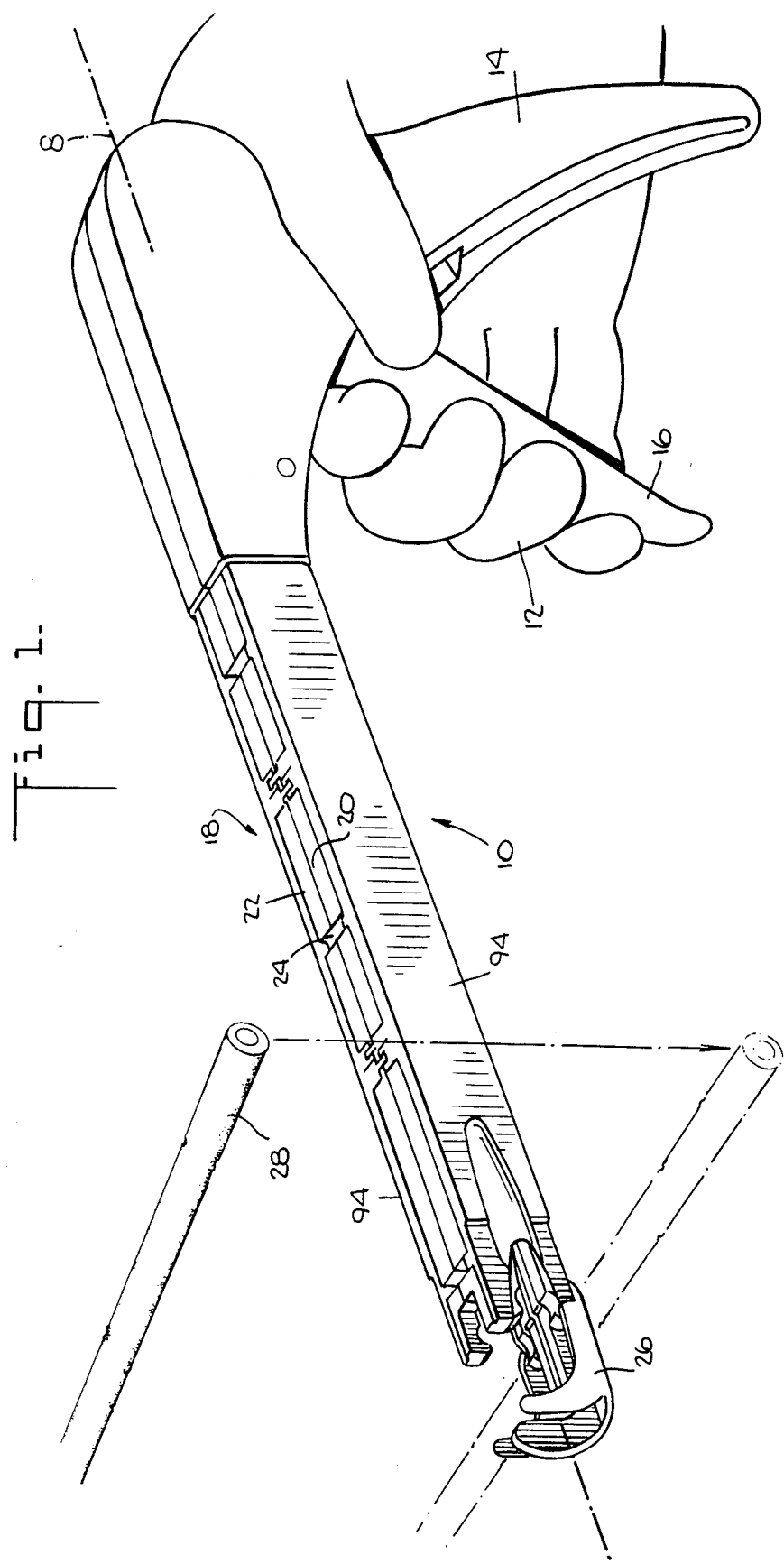
FIG. 1 is a perspective view of a surgical instrument in accordance with the present invention.

Before explaining the present invention in detail, it is to be understood that the invention is not limited in its applications or uses to the details of construction and arrangement of parts illustrated in the accompanying drawing, because the invention is capable of other embodiments, variations and modifications, and of being practiced or carried out in various ways. Furthermore, it is to be understood that the phraseology and terminology employed herein is for the purpose of description and illustration only, and is not for the purpose of limitation. For purposes of description herein, the same reference numerals are used to identify common elements shown in the various figures.

Referring now to FIG. 1, a surgical instrument for ligating and dividing in accordance with the present invention is shown generally at reference numeral 10. A hand 12 is shown gripping a handle 14 to which is attached a hollow trigger 16. Trigger 16 is shown in the open position, before a ligating and dividing surgical procedure is performed. Handle 14 forms part of the body of instrument 10, which also includes an actuating assembly.

A clip storage assembly is shown generally at reference numeral 18, and is attached to handle 14 by the actuating mechanism. Two tracks 20 and 22 run parallel to the longitudinal axis of instrument 10. The longitudinal axis is shown by broken line 8 in FIG. 1. The tracks have transverse channels 24 formed therein at spaced apart locations for receiving tabs on the metallic housing or wrap 94 of clip storage assembly 18 in order to secure the wrap to the channels.

A tissue gathering or tissue restraining assembly 26 is shown in its initial open position for receiving a tubular vessel 28, such as a blood vessel, duct, or other organic structure. The term tubular vessel as used herein is intended to connote an artery, a vein, an umbilical cord, a capillary, or any flexible and/or deformable tissue structure which is capable of being clamped and then severed.

Figure 2:
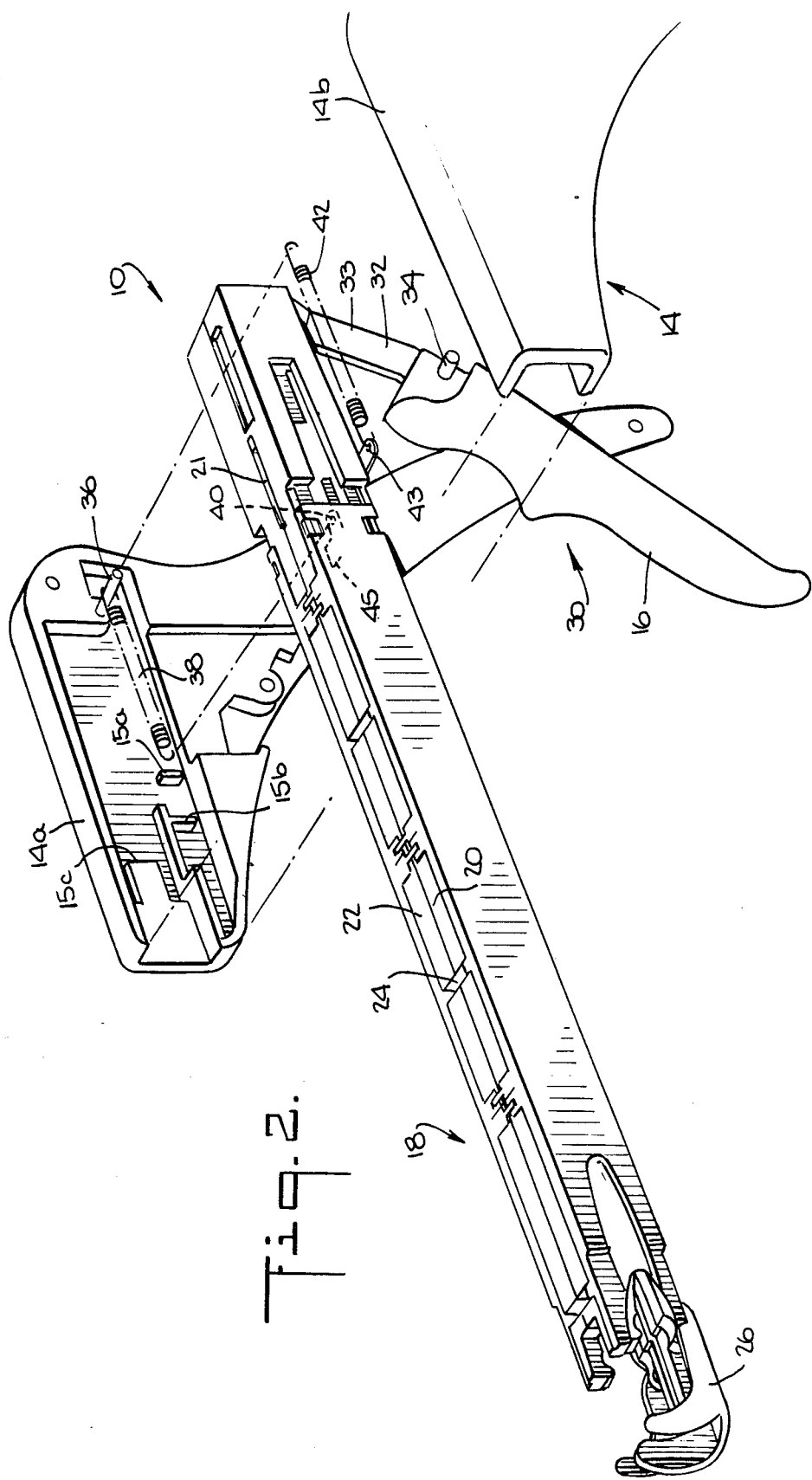
FIG. 2 is an exploded perspective view of part of the instrument of FIG. 1.

Referring now also to FIG. 2, an assembly view of part of instrument 10 illustrates the trigger assembly, shown generally at reference numeral 30. Trigger assembly 30 consists of hollow trigger 16 and trigger insert 32. Trigger insert 32 has an upper bar portion 33 and a lower portion, not shown in this figure, extending in and along substantially the entire length of hollow trigger 16. The lower portion of trigger insert 32 is fastened to hollow trigger 16 by rivets, glue, or other conventional means.

The body of instrument 10, which includes handle 14 and trigger 16, is manufactured from a plastic material such as ABS supplied by the Borg-Warner Company. Clip storage assembly 18 and tissue restraining assembly 26 are manufactured from a polycarbonate or similar material such as LEXAN polymer manufactured by the General Electric Company. Trigger assembly 30 has a pivot pin 34 by which the trigger assembly is mounted to handle 14.

Handle 14 consists of two halves 14a and 14b which are substantially identical mirror images of each other. Accordingly, instrument 10 is substantially symmetrical about a vertical plane that passes through longitudinal axis 8. There are some exceptions to the general bilateral symmetry of instrument 10. These exceptions will become apparent as the description proceeds.

Handle halves 14a and 14b are joined together by sonic welding or any other suitable means, such as by gluing or rivetting. The right half 14a of the handle has molded ribs 15a and 15b which are tissue restraining assembly bar stops. Both halves of handle 14 also have molded ribs 15c which are clip storage assembly stops (see also FIG. 15).

The right half 14a of the handle has a pin 36 which protrudes perpendicular to both the longitudinal vertical axis of handle 14 and the longitudinal axis 8 of instrument 10. Attached to pin 36 is one end of tissue restraining assembly return spring 38, which is a prestressed tension coil spring. The other end of spring 38 is connected to tissue restraining assembly spring retainer slot 40, shown in phantom. Slot 40 is formed in L-shaped tissue restraining assembly bar protrusion 45. Similarly, one end of knife return spring 42 is connected to pin 36. Spring 42 is another prestressed tension coil spring. The other end of spring 42 is connected to knife spring retainer slot 43.

Figure 3:
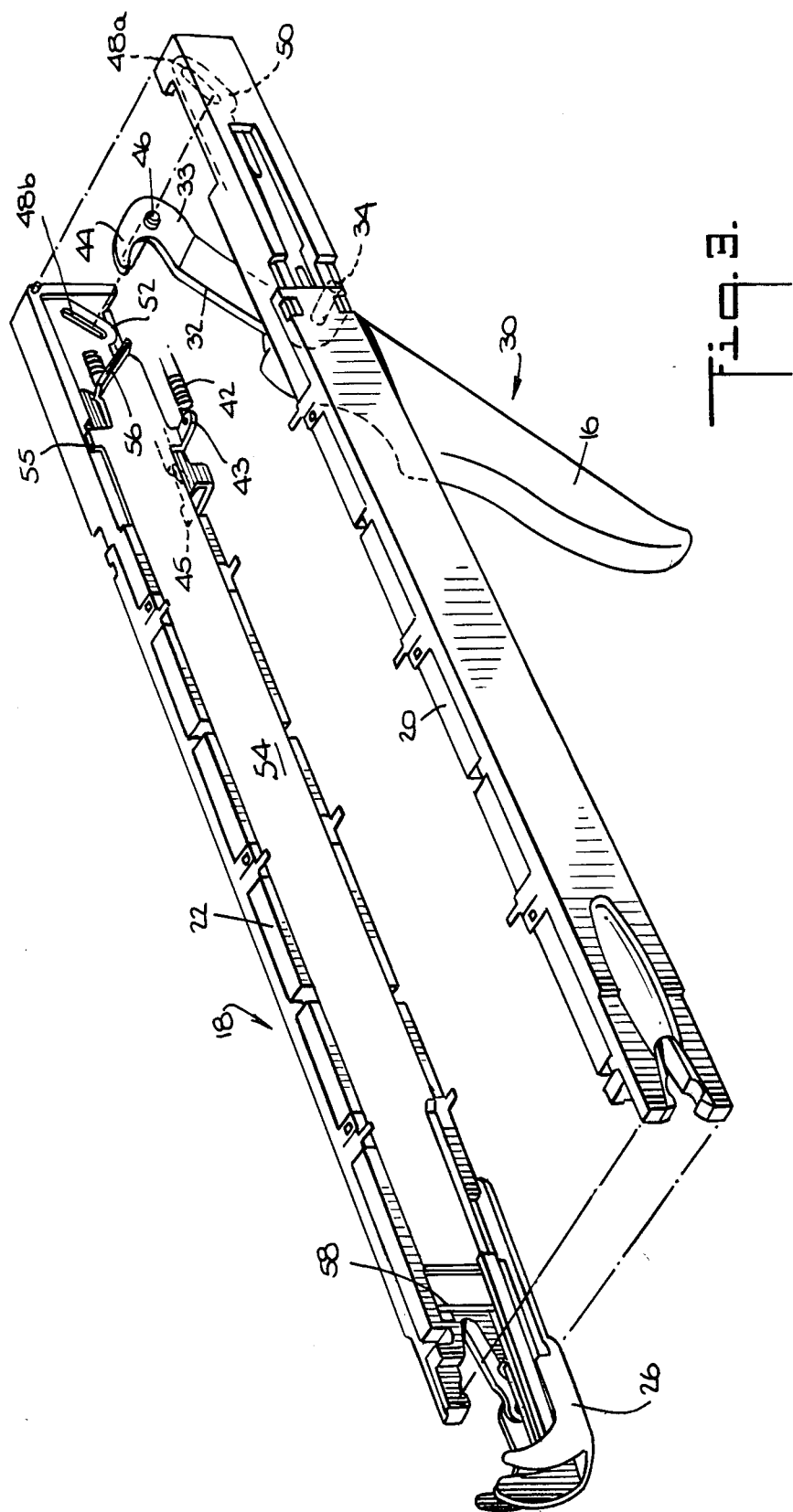
FIG. 3 is an exploded perspective view of the two tracks and trigger assembly of the instrument of FIGS. 1 and 2.

Referring now also to FIG. 3, trigger assembly 30 and its relation to tracks 20 and 22 of instrument 10 are shown.

The upper bar portion 33 of trigger insert 32 has a curved cam surface 44. The upper bar portion 33 also includes a pusher pin 46, attached by conventional means, which rides in slots 48a and 48b of a left pusher bar 50 and a right pusher bar 52, respectively. Pusher bars 50 and 52 are relatively thin metal beams disposed in, and housed by, left and right tracks 20 and 22. Slots 48a and 48b are elliptical cut-outs at the proximal end of pusher bars 50 and 52 and are both oriented so that the upper portion of each slot is more proximal than the lower portion.

A knife bar is shown at reference numeral 54 in the preferred embodiment. It will be appreciated, however, that a vessel may be divided in a number of ways besides knife or razor blade cutting, such as by laser or chemical destruction of tissue or by tearing. All such mechanisms for dividing are to be considered within the scope of the present invention.

A flange 56 is formed on knife bar 54 at the proximal end thereof. Knife bar 54 has a scalpel or knife blade 58 vertically attached to its distal end. Flange 56 is adapted to engage the curved cam surface 44 of upper bar portion 33 upon actuation of trigger assembly 30. Actuation of trigger assembly 30 occurs when a hand squeezes hollow trigger 16 toward handle 14, advancing upper bar portion 33 in a distal direction. Flange 56 is oriented generally opposite the right pusher bar slot 48b orientation. That is, the upper portion of flange 56 is more distal than the lower portion.

Clip storage assembly 18 includes (1) left track 20, housing left pusher bar 50, and (2) right track 22, housing right pusher bar 52. Also contained in clip storage assembly 18 is knife bar 54 with knife blade 58. Tissue restraining assembly 26 is also part of clip storage assembly 18. Only right track 22 is described in detail below. It should be understood that the structure and operation of left track 20 is similar to that of right track 22.

Referring now also to FIG. 4, the disassembled clip storage assembly 18 and a tissue restraining assembly bar 60 are shown. Tissue restraining assembly bar 60 is a metal beam positioned parallel to and between right pusher bar 52 and knife bar 54. Tissue restraining assembly bar 60 has a flange 62 for engaging pusher pin 46 (FIG. 3) of trigger assembly 30. Flange 62 is oriented at a similar angle to the right pusher bar slot 48b. That is, the upper portion of flange 62 is more proximal than the lower portion.

Referring now also to FIG. 5, tissue restraining assembly bar 60 is connected to tissue restraining assembly 26 for movement therewith by means of a vertical upward protrusion 63 in tissue restraining assembly 26 which engages a slot 64 in tissue restraining assembly bar 60. A vertical downward protrusion 66, distal-most on tissue restraining assembly bar 60, similarly engages a slot 68 in tissue restraining assembly 26.

A right pusher bar return spring 70, which is a prestressed compression coil spring, is compressed between right pusher bar 52 and stop surface 72 on right track 22.

Referring now also to FIG. 6, tissue restraining assembly 26 has a lower tissue restraining assembly surface 74 which is adapted to slide along rails 76 of right track 22 and left track 20, not shown in this figure.

Referring now also to FIG. 7, right pusher bar 52 is shown in greater detail. Right pusher bar 52 has a spring retainer 78, parallel to the longitudinal axis of clip storage assembly 18, for positioning the proximal end of right pusher bar return spring 70. Temporarily positioning the distal end of right pusher bar return spring 70 prior to assembly of the apparatus is another spring retainer 80, also parallel to the longitudinal axis of clip storage assembly 18, which is part of right pusher bar 52. When the apparatus is assembled, the distal end of spring 70 bears on stop surface 72, which is part of right track 22.

On the distal side of stop surface 72 is an anti-jamming mechanism 81. The anti-jamming mechanism, which is described in greater detail below with references to FIGS. 10 and 10a, includes (1) a flag 82, which is part of right pusher bar 52, and (2) a ramp assembly 84 connected to right track 22. A clip spring holder, also described in greater detail below with reference to FIG. 8, is shown at reference numeral 85.

Referring now also to FIG. 8, surgical ligatures or clips 86 of plastic-like material are individually dispensable but shown interlocking in a clip stack or train. Clips 86 in the preferred embodiment are made from a biologically absorbable copolymer which is a polyester derivative of lactide and glycolide. Such material is absorbable by the body and is radiotransparent. These clips 86 are further described in co-pending, commonly assigned U.S. patent application Ser. No. 436,056, filed Oct. 22, 1982 and entitled "Polymers for Injection Molding of Absorbable Surgical Devices". Of course, any plastic or plastic-like material which can be formed into suitable clips, regardless of whether it is absorbable by the body, can be used. Such material may be, for example, polyester, polyamid, and the like. All such materials are generically referred to herein as plastic-like materials.

Clips 86 releasably interlock with each other as described hereinbelow with regard to FIG. 21 and in commonly assigned, co-pending U.S. patent application Ser. No. 429,250, filed Sept. 30, 1982 and entitled "Surgical Clip Applying Methods and Apparatus, and Clips and Clip Train for Use Therein". Clips 86 are adapted to be pushed sequentially by the end of a clip pusher 92, which is the distal-most end of right pusher bar 52 and which pushes on the base of the distal-most clip in the train. The proximal-most one of clips 86 is seated in a U-shaped clip guide 88. Clip guide 88 prevents the last one or two clips in the train from becoming skewed in the apparatus after all of the preceding clips have been used. A compression coil spring 90 is prestressed between clip guide 88 and clip spring holder 85 (FIGS. 7 and 10) to give the clip train an initial boost in the distal direction. After two or three clips have been used, spring 90 serves no further purpose.

Referring now also to FIG. 9, there is illustrated a bottom view of instrument 10, showing the assembled left and right tracks 20 and 22, and a relatively thin metal housing or wire wrap 94 enclosing them. The two sides of wire wrap 94 are attached to one another by interlocking protrusions 96 and slots 98. A safety mechanism 100 is shown in phantom in this figure, and is described in more detail below.

Tissue restraining assembly 26 has a cutting post or tube 102 against which knife blade 58 (FIG. 3) is forced during a dividing operation. Cutting post 102 is preferably a hollow cylindrical section manufactured from PVC material.

Referring now also to FIG. 10, there is shown the assembly of right track 22, including the right side of wire wrap 94, right pusher bar 52 with right pusher bar return spring 70, a cover 106 for isolating the operation of right pusher bar 52 from the clip train, the stack of interlocking clips 86, clip guide 88, guide spring 90 which fits over a post 108 on clip guide 88, clip spring holder 85, and an interior wall 91 of right track 22, including ramp 84 and a clip positioning pawl 110 toward the distal-most end of interior wall 91. The operation of pawl 110 is described in detail below with reference to FIGS. 24 et seq. Cover 106 has a pair of detents or resistance dimples 107 formed therein for helping to uncouple the distal-most clip from the clip train as described in detail below.

Referring now also to FIG. 11, the actuation assembly is shown generally at reference number 112. Actuation assembly 112 includes trigger assembly 30, knife bar 54, right pusher bar 52, left pusher bar 50 and the associated pusher bar return spring (not shown in this figure), pusher pin 46, knife return spring 42, and right pusher bar return spring 70.

Referring now also to FIG. 12, there are shown the two tracks 20 and 22. Between tracks 20 and 22 are vertical knife blade 58 and tissue restraining assembly bar 60. The end portions of right and left clips 86 are also shown in this drawing, disposed in left and right channels 114 and 116, respectively. Channels 114 and 116 are formed by covers 106, which isolate operation of pusher bars 50 and 52 (FIG. 3), and interior walls 91. A train of clips 86 is contained within each of channels 114 and 116.

Referring now also to FIG. 13, instrument 10 is shown when a cycle of ligating and dividing is completed but before trigger assembly 30 is released. FIG. 14 is a view of the distal-most end of instrument 10 taken along the line 14—14 in FIG. 13.

In order to describe the operation of instrument 10 in stages during a complete surgical procedure, reference should also now be made to remaining FIGS. 15-30.

In operation, discrete stages of activity occur when trigger 16 is squeezed toward handle 14. Thus, reference should be made to the previous figures, especially FIG. 11, which illustrates the position of each of the elements before a ligating and dividing cycle is initiated.

Referring now also to FIG. 15, before the surgical procedure begins, tissue such as tubular vessel 28 is placed in tissue restraining assembly 26 of instrument 10. Knife bar 54 and blade 58, as well as left and right pusher bars 50 and 52 and left and right tracks 20 and 22 are all in their proximal-most or retracted positions. Tissue restraining assembly 26 is also in its proximal-most position. At this point, trigger 16 (FIG. 11) is in its open position.

Referring now also to FIG. 16, as trigger 16 is squeezed toward handle 14 to a position approximately 36% of the way closed, trigger assembly 30 is rotated counter-clockwise about pivot 34. Such rotation forces both ends of pusher pin 46 on trigger insert 32 to move in their respective slots 48a and 48b in left and right pusher bars 50 and 52, respectively. Thus pusher bars 50 and 52 are forced to begin to move distally. The prestress compression force exerted by right pusher bar return spring 70 (FIG. 5) and left pusher bar return spring (not shown) is less than the prestress tension force exerted by knife return spring 42. Accordingly, left and right tracks 20 and 22 move with pusher bars 50 and 52, and the entire housing advances distally relative to tissue restraining assembly 26 to close around and grip tissue 28 between tissue restraining assembly 26 and the rest of clip storage assembly 18. Knife bar 54 and knife blade 58 move distally with tracks 20 and 22 because upward projection 55 (FIG. 4) on knife bar 54 bears against the proximal end of slot 21 (FIG. 2) which is formed between tracks 20 and 22. Knife return spring 42 is extended during distal movement of tracks 20 and 22 as described above, but tissue restraining return spring 38 does not extend during this phase of the operating cycle of the apparatus.

When trigger 16 has been squeezed approximately 36% of the way towards a closed position relative to handle 14, the tissue locking operation is completed, as shown in FIG. 16. Tracks 20 and 22 come to rest against stops 15c. Further squeezing of handle 14 causes pusher bars 50 and 52 to move distally relative to tracks 20 and 22 as shown in FIG. 17. This begins to compress right pusher bar return spring 70 and also causes clip pusher 92 to begin to advance the distal-most clip 86 relative to track 22. Of course, the same events are occurring simultaneously on the left-hand side of the instrument.

Shortly after pusher bars 50 and 52 begin to move distally relative to tracks 20 and 22, the camming surface 44 of the upper bar portion 33 of trigger insert 32 begins to engage flange 56 of knife bar 54. This begins to force knife bar 54 to advance distally toward tissue 28 and tissue restraining assembly 26 as shown in FIG. 17. Knife bar 54 advances at a greater rate of speed than pusher bars 50 and 52. Knife return spring 42 extends accordingly.

Just before the stage shown in FIG. 18 is reached, pin 46 contacts the proximal flange 62 of tissue restraining bar 60 (FIG. 4). This initiates distal motion of bar 60 and tissue restraining assembly 26 so that by the stage shown in FIG. 18, L-shaped tissue restraining assembly bar protrusion 45 has moved a distance "d" from stop 15a, and tissue restraining assembly 26 has moved a similar distance "d" relative to tracks 20 and 22. Tissue restraining assembly return spring 38 (FIG. 2) is extended by distal motion of tissue restraining assembly bar 60.

Clips 86 are then formed, as described in greater detail below, to close around tissue 28, ligating it at two spaced apart locations. Tissue restraining assembly bar 60 and tissue restraining assembly 26 move distally during this phase of the procedure so that closed clips 86 can be fully ejected from the clip forming jaws described in detail below without causing the tissue to stretch prior to cutting.

As trigger 16 is squeezed still farther toward handle 14, knife blade 58 cuts tissue 28 against tube 102, as shown in FIG. 19. During the cutting operation, knife bar 54 and blade 58 force tube 102 of tissue restraining assembly 26 to move distally, separating tissue restraining assembly bar 60 from pin 46. Thus, pin 46 no longer engages tissue restraining assembly bar 60, but tissue restraining assembly 26 nevertheless continues to be forced distally by knife bar 54 and blade 58. The two closed clips 86 are completely ejected from the clip forming jaws described below. Tissue restraining assembly bar 60 stops moving distally when L-shaped protrusion 45 contacts tissue restraining assembly bar stop 15b. This coincides with trigger 16 being fully closed.

When trigger 16 is released from its closed position relative to handle 14, all components of the instrument return to their initial positions in response to the forces produced by springs 38, 42, and 70. Tissue restraining assembly 26 does not move proximally as far as tracks 20 and 22, thereby allowing tissue 28 and its attached clips 86 to be removed from instrument 10.

Referring now also to FIG. 20, the safety mechanism 100 further described hereinbelow, is shown blocking passage of knife blade 58 when a mis-feed of a clip 86 occurs in right track 22.

Figure 21:
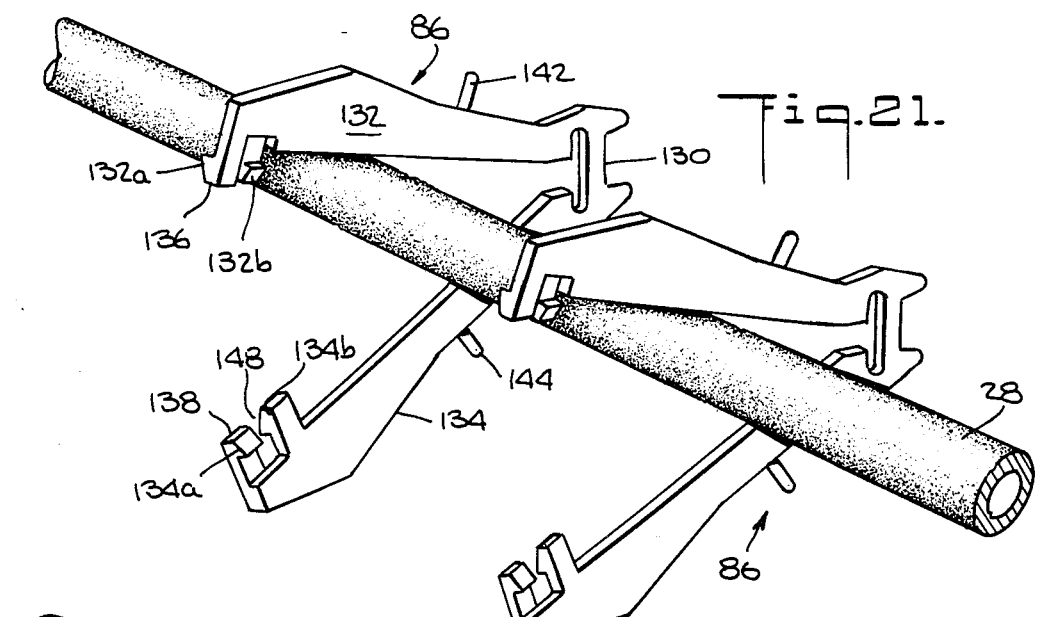
FIGS. 21–23 are perspective views of three successive stages in a ligating and dividing operation using surgical clips.
Figure 22:
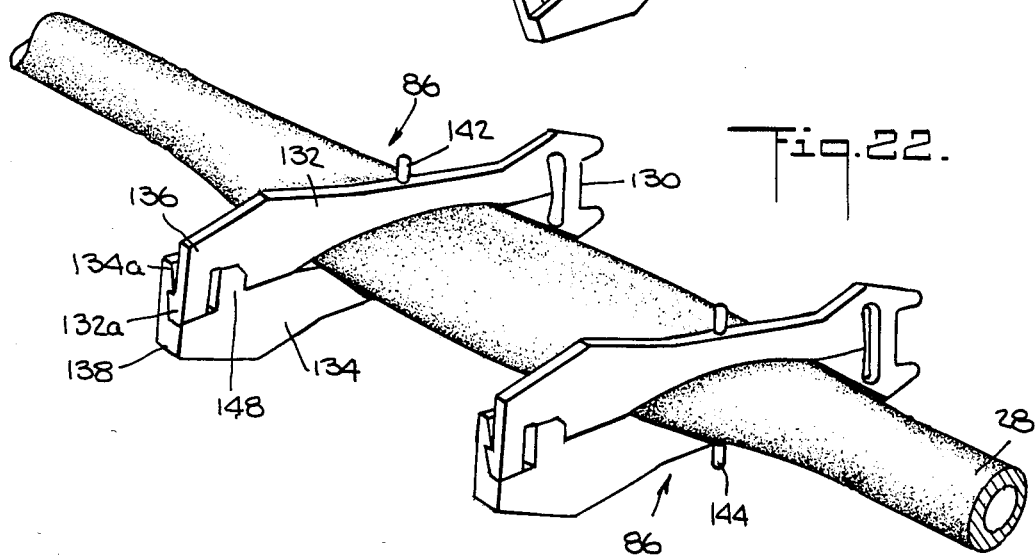

Referring now also to FIGS. 21 and 22, illustrative ligatures or clips 86 are shown. Each clip 86 includes a base 130 and two arms 132 and 134 extending from respective opposite ends of the base. The base 130 and arms 132 and 134 of each clip 86 lie in a common plane. Each clip 86 is made so that the normally free end portions 136 and 138 of arms 132 and 134 are resiliently biased apart. Laterally extending lugs 142 and 144 are respectively located along arms 132 and 134. The inner periphery of the normally free end portion 136 and 138 of each arm 132 and 134 includes a slot 146 and 148, respectively.

When the physically separate and individual clips 86 are associated with one another in a train, as shown for example in FIG. 10, the lugs 142 and 144 of each clip 86 are respectively releasably received in and engaged by the slots 146 and 148 in the immediately following clip 86. The arms 132 and 134 of each clip 86 are prevented from spreading farther apart by the surrounding structure of instrument 10. Accordingly, when the distal-most clip 86 in the train is pushed in the distal direction as described in detail below, all of the succeeding clips 86 in the train are pulled along at the same time.

Resistance dimples 107 (FIG. 10) retard advancement of the rest of the clip train as the distal-most clip 86 is advanced, thus helping to uncouple the distal-most clip from the clip train.

The normally free end portions 136 and 138 of the arms of each clip 86 also include complementary latching elements 132a and 132b on arm 132 and 134a and 134b on arm 134. When the arms 132 and 134 of the clip 86 are squeezed together as shown in FIG. 22, latching elements 132a and 134a overlap and interlock with one another, and latching elements 132b and 134b similarly overlap and interlock with one another. Once these latching elements interlock, they hold clip 86 closed. The sense or direction of the overlap of latching elements 132a and 134a is opposite to the sense or direction of the overlap of latching elements 132b and 134b. This makes the clip 86 highly resistant to inadvertent reopening by helping to keep arms 132 and 134 co-planar.

Figure 23:
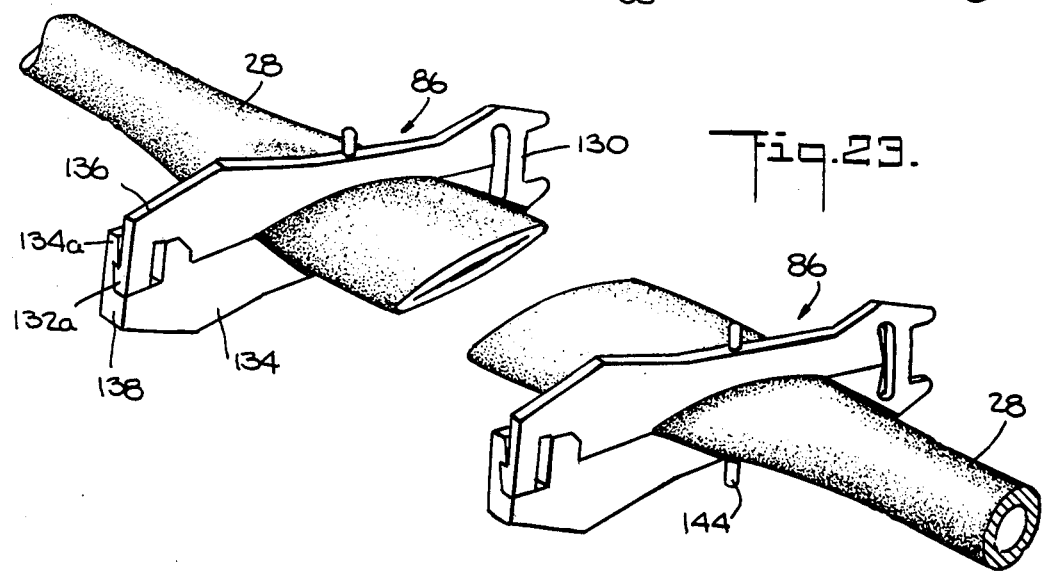

FIG. 23 shows the position of two closed clips 86 after a tubular vessel 28 has been ligated at two spaced apart locations and divided intermediate the clips 86.

Clips 86 may have various sizes depending on their intended use. Typical clips may be about 10 mm long and 8 mm wide before being closed. Much smaller clips may be used for certain applications in microsurgery. Larger clips may be used for other purposes such as closing oviducts and vas deferens. Instrument 10 is sized appropriately for the clips it is to apply.

Referring now also to FIGS. 24-28, operation of the distal end of instrument 10, and more particularly clip storage assembly 18, is shown during the stages of a tissue ligating and dividing surgical procedure. Closure or forming of surgical clips 86 by means of forcing them through fixed jaws of a surgical instrument is explained in detail in commonly assigned, co-pending U.S. patent application Ser. No. 429,249, filed Sept. 30, 1982 and entitled "Surgical Clip Applying Apparatus Having Fixed Jaws".

Figure 24:
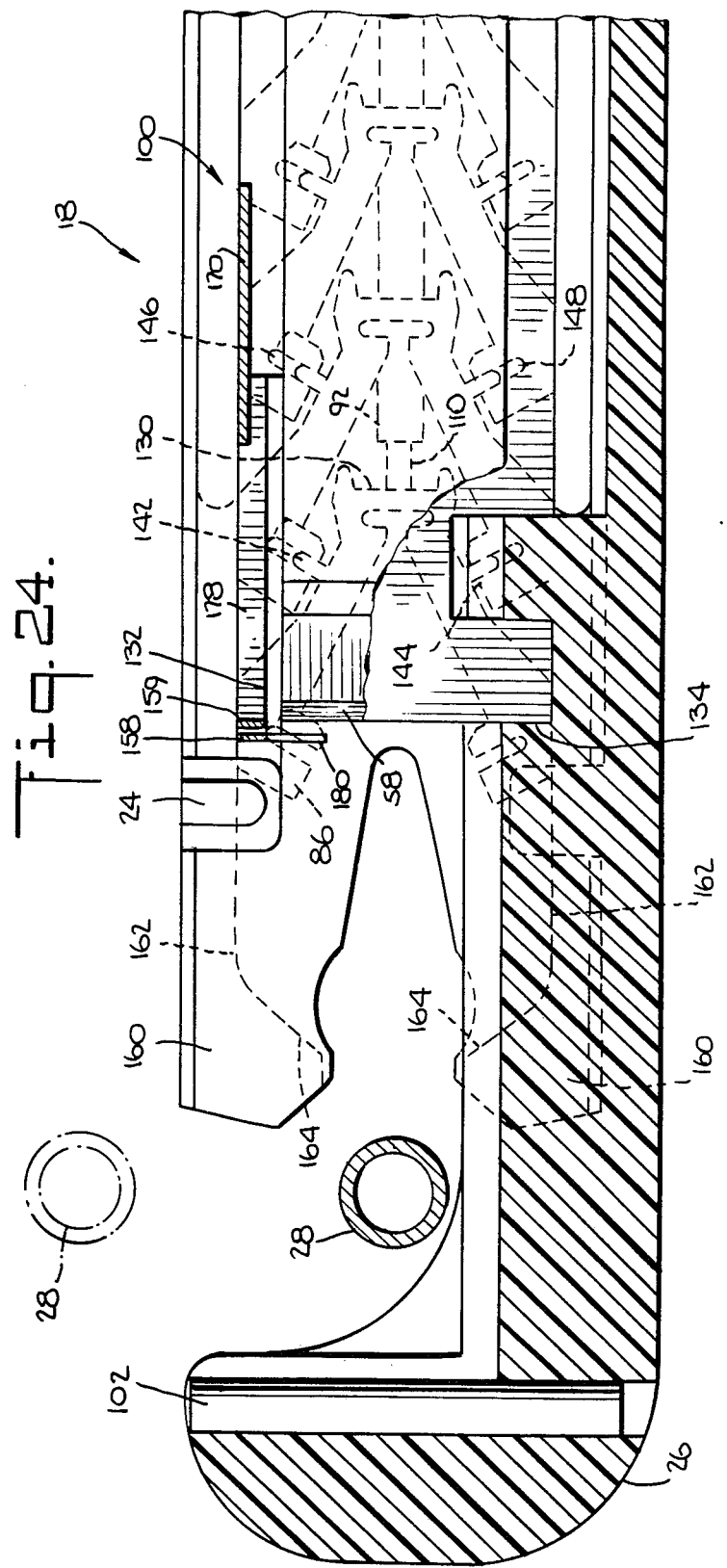
Figure 25:
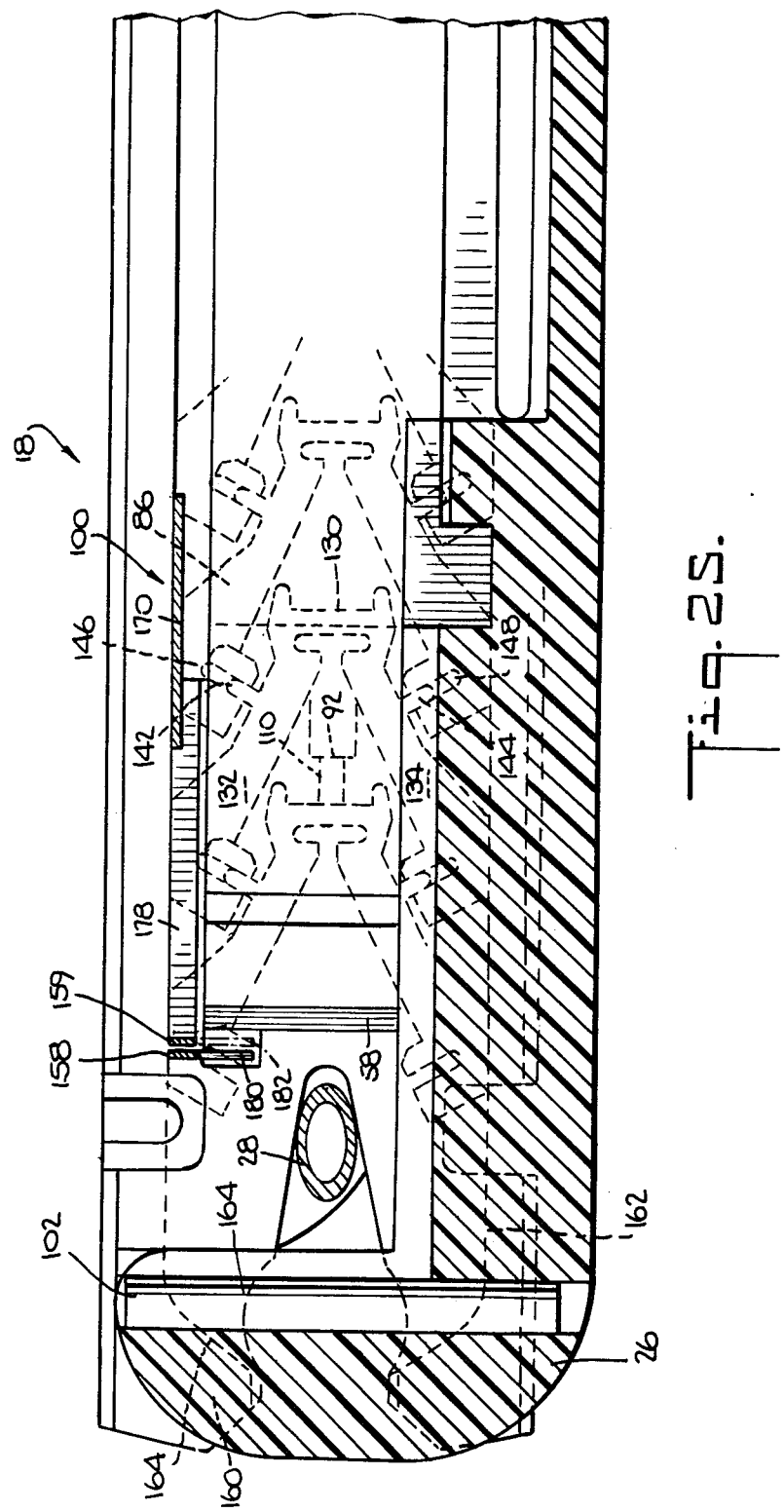

The initial condition of the apparatus is shown in FIG. 24. A plurality of clips 86 are coupled together in two trains as described above and disposed in left and right channels 114 and 116 (FIG. 12) with the open side of each clip 86 facing in the distal direction toward a set of jaws 160, shown in phantom, oppositely disposed in each channel 114 and 116. One set of jaws 160, consisting of an upper and lower member, is disposed in each channel 114 and 116. Thus, there are four jaw members 160 in clip storage assembly 18.

The base 130 of the distal-most clip 86 in the train in channel 116 is initially on the distal side of clip pusher 92 and pawl 110. The bases 130 of all the other clips 86 in channel 116 are on the proximal side of clip pusher 92 and pawl 110. Right pusher bar 52 is in its proximal-most position, which corresponds to trigger 16 and handle 14 (FIG. 1) being at their maximum separation (i.e., 0% of the way towards a closed position). The left side of the apparatus, which is not described in detail herein, is constructed and operates similarly.

Two flag stop assemblies 158 and 159 are each disposed perpendicular to knife blade 58 (FIG. 3) and on either side thereof for a hereinafter described purpose.

When clips 86 are required, the body tissue 28 to be ligated is positioned between jaws 160 and the distal-most portion of tissue restraining assembly 26, as shown in FIG. 24. As trigger 16 and handle 14 are squeezed together, right pusher bar 52 is driven in the distal direction. As right pusher bar 52 moves distally, right clip pusher 92 moves distally past the distal end of clip positioning pawl 110 (compare FIGS. 25 and 26; see also FIGS. 16 and 17), contacts the proximal side of the base 130 of distal-most clip 86, and advances that clip in the distal direction along its channel 116. All of the other clips in the train are pulled along with the distal-most clip. An identical procedure occurs, of course, on the left side of the instrument in the left track 20.

Figure 26:
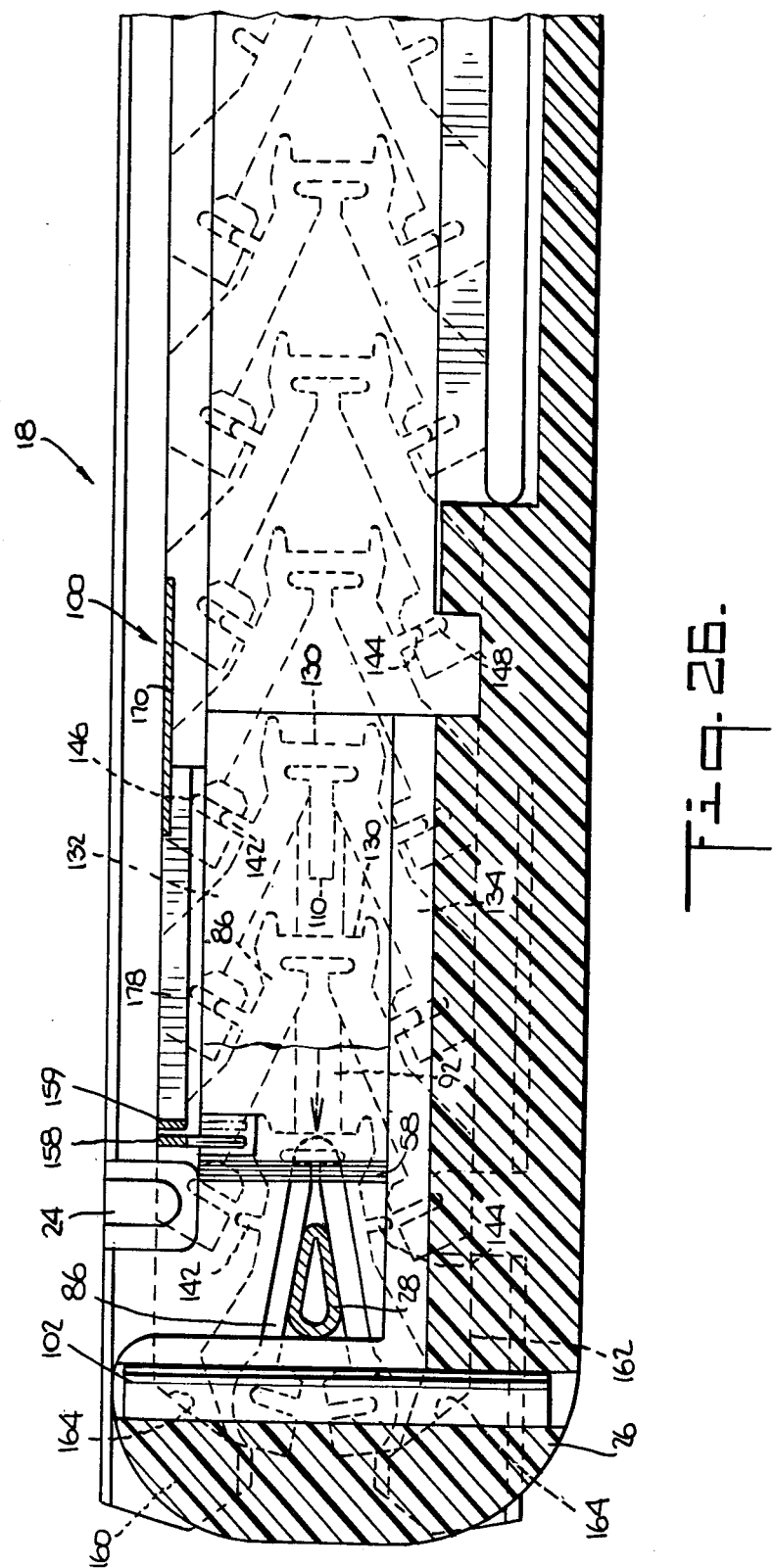

As shown in FIG. 26, each arm 132 and 134 of the distal-most clip 86 enters a respective one of jaws 160 so that an arm of each clip is on each side of tissue 28. Each of jaws 160 has a longitudinal jaw channel 162 for receiving and guiding an arm of a clip 86. Jaw channels 162 keep their respective clips 86 in the proper orientation in the instrument until the clips 86 have been closed.

When the distal-most portions of the initially free ends of arms 132, 134 of the distal-most clip 86 contact converging jaw surfaces 164, arms 132 and 134 begin to deflect or pivot toward one another so that the clip 86 begins to close on the tissue 28. As arms 132 and 134 converge toward one another, lugs 142 and 144 on the distal-most clip 86 disengage from slots 146 and 148 respectively in the next-to-distal-most clip 86, thereby uncoupling the distal-most clip 86 from the remaining clips in the train. To aid in the uncoupling operation, resistance dimples 107 (FIG. 10) engage arms 132 and 134 of the succeeding clip proximate the distal-most clip 86, retarding further distal motion of the next-to-distal-most clip. This uncoupling of the distal-most clip occurs after the base 130 of the next-to-distal-most clip has moved to the distal side of the distal end of pawl 110 but before the base 130 of another clip has moved to the distal side of the distal end of pawl 110. This assures that one clip, and only one clip, is advanced to jaws 160 on each side of knife blade 58 during each operating cycle of the instrument.

As trigger 16 and handle 14 continue to be squeezed together, right pusher bar 52 and clip pusher 92 continue to push distal-most clip 86 farther into jaws 160. Converging jaw surfaces 164 continue to force arms 132 and 134 of the distal-most clip 86 together.

When the instrument 10 reaches the condition shown in FIG. 27, distal-most clip 86 is fully closed and latching elements 132a and 132b (FIG. 21) respectively interlock with latching elements 134a and 134b to hold the clip closed. Preferably, closed clip 86 exerts sufficient pressure on tissue 28 to provide hemostasis without causing undue tissue damage.

Anti-jamming mechanism 81 (FIGS. 7, 10, and 10a) is provided to prevent another clip 86 from being advanced in either of channels 114 and 116 until the preceding clips have been completely closed and ejected from those channels. When an operating cycle begins, flag 82 is located relative to ramp assembly 84 as shown in FIG. 7 and at reference number 82a in FIG. 10a. When pusher bar 52 begins to advance relative to track 22, flag 82 moves to position 82b in FIG. 10a shortly after the distal end of clip pusher 92 moves distally past the distal end of pawl 110. In position 82b, latch surface 83 on ramp assembly 84 prevents flag 82 from retracting in the proximal direction, even if trigger 16 is prematurely released. This prevents clip pusher 92 from retracting to a position proximal of the distal end of pawl 110 and thereby picking up another clip until after the clip which pusher 92 has already begun to advance has been completely closed and ejected from the instrument.

As clip pusher 92 is ejecting a completely closed clip from jaws 160 as described in detail above, flag 82 passes around the distal end of ramp assembly 84 as shown at position 82c in FIG. 10a. When trigger 16 is released following ejection of the closed clip, flag 82 traverses the opposite side of ramp assembly 84 as shown in part by the reference number 82d in FIG. 10a and returns to its initial position 82a when the remainder of the instrument returns to its initial condition.

From the foregoing, it will be seen that anti-jamming mechanism 81 prevents double feeding of clips, which could cause the apparatus to malfunction and jam.

Referring now also to FIG. 29, safety mechanism 100 is positioned at a distal location in clip storage assembly 18. Safety mechanism 100 prevents tissue 28 (FIG. 1) from being divided before it is ligated at both sides of the intended dividing point. In ligating and dividing surgical procedures, it is often important that a tubular vessel such as a blood vessel first be successfully ligated at two locations before it is divided intermediate those locations. If either one or both ligatures fail to function properly, hemorrhaging, the uncontrolled flow of fluid (e.g., blood) from the vessel, will result upon division of the vessel.

Safety mechanism 100 has a substantially flat base 170 which is perpendicular to the planes defined by the left and right tracks 20 and 22 and parallel to the longitudinal axis 8 of the instrument. Base 170 spans both tracks 20 and 22 and knife bar 54. Base 170 has a manufacturing detent 172 on each side to facilitate maintaining a relatively clean surface upon bending of the safety mechanism extremities. Base 170 of safety mechanism 100 rests on interior walls 91. Safety mechanism 100 remains stationary with respect to tracks 20 and 22 and is prevented from moving distally during operation of instrument 10.

Attached to either side of base 170 are arms 176 and 178 which extend along the longitudinal axis of clip storage assembly 18. Arms 176 and 178 are biased outwardly and extend into the upper portion of right and left clip channels 114 and 116, respectively. Arms 176 and 178 are in close proximity to covers 106. When surgical clips 86 are placed in channels 114 and 116, however, safety mechanism arms 176 and 178 contact upper clip arms 132 and are thereby forced inwardly toward centrally located knife bar 54 and blade 58.

The free end of each arm 176 and 178 is bent substantially perpendicular to the longitudinal axis 8 of instrument 10. At the free end of the arms 176 and 178 are flags 180 and 182, respectively, which extend downwardly to block advancement of knife bar 54 and blade 58 when either of safety mechanism arms 176 or 178 is in close proximity to cover 106. Flags 180 and 182 overlap and therefore do not interfere with the operation of one another. This is due to the fact that right safety mechanism arm 178 is bent in a protruded U-shaped hinge 184 to allow flag 182 attached to right arm 178 to be positioned more proximally than flag 180 in clip storage assembly 18. To prevent skewing, however, both safety mechanism arms 176 and 178 are adapted, by means of the same protruded U-shaped hinge 184, to contact clips 86 at substantially the same distance from the distal-most end of instrument 10.

In operation, as a clip 86 advances along right clip channel 116, for example, it forces the free end of right safety mechanism arm 178 to move toward knife bar 54. Right flag 182 advances out of the direct path of knife blade 58 to allow blade 58 to continue its advancement to engage tissue 28.

Similarly, as a clip 86 advances along left channel 114, left safety mechanism arm 176 is also deflected toward knife bar 54, forcing left flag 180 to move out of the direct path of knife blade 58.

FIG. 30 illustrates operation of safety mechanism 100 when a surgical clip 86 is misfed in right channel 116. Right safety mechanism arm 178 remains in close proximity to cover 106. Right flag 182 remains in its normally undeflected position, directly blocking the advancement of the distal edge of the knife bar 54 and blade 58. Of course, safety mechanism 100 operates in a like manner when all surgical clips 86 have been successfully ejected from instrument 10. Accordingly, a dividing operation can occur only after a ligating operation has been successfully performed.

Since other modifications and changes varied to fit particular operating requirements and environments will be apparent to those skilled in the art, the invention is not considered limited to the examples chosen for purposes of disclosure, and covers all changes and modifications which do not constitute departures from the true spirit and scope of this invention. For example, clips 86 can be made of plastic-like materials which are biologically absorbable or nonabsorbable as discussed in detail above.

I claim:

1. Apparatus for ligating and dividing an organic tissue structure comprising:

means for simultaneously applying two clips of plastic-like material around the tissue structure at two spaced apart locations along the tissue structure to ligate the tissue structure at the locations of the clips, said means including first and second substantially parallel laterally spaced clip applying assemblies, each assembly containing a respective one of said clips, and each assembly including (1) a pair of jaws rigidly fixed relative to one another forming a discharge opening and disposed on respective opposite sides of the tissue structure and (2) means for forcing the associated clip completely through the jaws of the assembly so that the clip closes one to the fixed relationship of the jaws as it is forced through said discharge opening; and means for cutting the tissue structure between the clips.

2. The apparatus defined in claim 1 further comprising means for holding the tissue structure between the jaws of each clip applying assembly while the clips are being applied around the tissue structure.

3. The apparatus defined in claim 2 further comprising:

first means for moving the jaws of each clip applying assembly relative to the tissue holding means prior to pushing the clips through the jaws so that the tissue is positioned between the jaws of each clip applying assembly prior to pushing the clips through the jaws.

4. The apparatus defined in claim 3 further comprising:

second means for moving the tissue holding means relative to the jaws of each clip applying assembly so that as the clips are applied around the tissue structure, the tissue holding means and the clips move with one another to prevent the tissue holding structure from impeding ejection of the clips from the jaws or stretching the tissue structure as the clips are ejected from the jaws.

5. The apparatus defined in claim 4 further comprising:

actuator means having a single manually operable trigger mechanism; and sequencing means responsive to operation of the trigger mechanism for first operating the clip applying means, and then operating the tissue cutting means.

6. The apparatus defined in claim 5 further comprising:
means for maintaining the tissue holding means stationary relative to the actuator means until the clips are being ejected from the jaws; and
means for moving the tissue holding means relative to the actuator means and with the clips as the clips are being ejected from the jaws.

7. The apparatus defined in claim 6 wherein the tissue cutting means comprises:
knife means initially disposed on the side of the jaws remote from the tissue holding means;
knife anvil means mounted on the tissue holding means; and
means responsive to the sequencing means for moving the knife means from its initial position to a position in which the knife means engages the knife anvil means whereby the knife means cuts the tissue against the knife anvil means.

8. The apparatus defined in claim 7 wherein the means for moving the knife means moves the knife means faster than the means for moving the tissue holding means moves the tissue holding means.

9. The apparatus defined in claim 1 wherein the apparatus is capable of repeated operation, and wherein each clip applying assembly comprises:
a clip magazine for storing a plurality of clips of plastic-like material; and
means for advancing the clips one at a time in succession from the clip magazine to the associated jaws.

10. The apparatus defined in claim 9 wherein the clips are stored in each magazine in a train in which each clip is releasably coupled to the succeeding clip in the train.

11. The apparatus defined in claim 10 wherein each means for advancing the clips comprises:
reciprocating pusher means for contacting the clip closest to the associated jaws and pushing that clip into the associated jaws, each of the other clips in the associated train being pulled along by the preceding clip in the train;
means for uncoupling from the train the clip closest to the associated jaws as the pusher means pushes that clip into the jaws;
means for retracting the pusher means to the next clip in the train after the first clip has been pushed into the jaws; and
means for preventing the clip train from retracting when the pusher means is retracted.

12. The apparatus defined in claim 11 further comprising:
means for preventing the pusher from retracting to the next clip until the preceding clip has been pushed completely into the jaws.

13. Apparatus for ligating and dividing an organic tissue structure comprising:
first and second substantially parallel, laterally spaced clip applying assemblies, each assembly containing a plurality of clips of plastic-like material, and each assembly including (1) a pair of jaws that are rigidly fixed relative to one another and spaced apart for receiving the tissue to be ligated between the jaws and (2) means for forcing the associated clips through the jaws of the assembly one at a time in succession so that the jaws close each clip as the clip is forced through the jaws;
tissue supporting means movably mounted relative to the clip applying assemblies;
actuator means for sequentially causing (1) relative motion of the tissue supporting means and the clip applying assemblies toward one another, prior to forcing a clip through the jaws of each assembly, in order to position the tissue to be ligated between the jaws of both assemblies, and (2) relative motion of the tissue supporting means and the clip applying assemblies away from one another, after forcing a clip into the jaws of each assembly and thereby closing the clips on the tissue, in order to facilitate ejection of the clips from the jaws; and
means for cutting the tissue between the clips after the clips have closed on the tissue.

14. The apparatus defined in claim 13 wherein the means for forcing the clips through the jaws of each clip applying assembly comprises:
means for pushing the clip which is closest to the jaws of the assembly through the jaws;
means associated with each clip in the assembly for releasably coupling that clip to the succeeding clip so that the clips form a train which moves with the clip closest to the jaws until the clip closest to the jaws enters the jaws, at which time the clip entering the jaws uncouples from the train; and
means for substantially preventing the train from moving away from the jaws after the clip entering the jaws uncouples from the train.

15. The apparatus defined in claim 13 wherein each clip comprises two initially divergent arms pivotally connected to one another adjacent a first end of each arm, and means adjacent the second end of each arm for holding the arms together when the clip is closed.

16. The apparatus defined in claim 13 wherein the plastic-like material of the clips is biologically absorbable.

17. The apparatus defined in claim 13 wherein the actuator means includes:
first means for holding the tissue supporting means stationary relative to the user of the apparatus until a clip has been forced into the jaws of each assembly; and
second means for holding the jaws stationary relative to the user of the apparatus after a clip has been forced into the jaws of each assembly.

18. The apparatus defined in claim 13 wherein the means for cutting the tissue comprises:
a knife blade mounted between the clip applying assemblies for reciprocal motion substantially parallel to the assemblies; and
a knife anvil mounted on the tissue supporting means so that the knife blade cuts the tissue against the knife anvil.

19. Apparatus for ligating and dividing an organic tissue structure comprising:
a body;
an actuator movably mounted relative to the body;
clip applying means including (1) first and second parallel, laterally spaced, relatively fixed clip applying assemblies movably mounted relative to the body, each assembly containing a plurality of clips of plastic-like material, and each assembly having (a) a pair of jaws that are rigidly fixed relative to one another and spaced apart for receiving the tissue to be ligated between the jaws and (b) means for forcing the associated clips through the jaws of the assembly one at a time in succession so that the jaws close each clip on tissue disposed between the jaws as the clip is forced through the jaws, (2) tissue supporting means movably mounted relative to the clip applying assemblies, and (3) knife means disposed intermediate the clip applying assemblies and movably mounted relative thereto; and means responsive to motion of the actuator for sequentially causing (1) the clip applying assemblies to move toward the tissue supporting means to position the tissue to be ligated between the jaws, (2) a clip to advance into the jaws of each clip applying assembly and to close on the tissue, and (3) the closed clips to be ejected from the clip applying assemblies and concurrently the knife means to cut through the tissue between the clips and the tissue supporting means to move away from the clip applying assemblies to facilitate ejection of the clips.

20. The apparatus defined in claim 19 wherein the means responsive to motion of the actuator includes means for keeping the tissue supporting means stationary relative to the body at least until the clips have substantially closed on the tissue.

21. The apparatus defined in claim 20 wherein the means responsive to motion of the actuator includes means for keeping the jaws stationary relative to the body while the clips are being forced through the jaws.

22. The apparatus defined in claim 19 wherein the tissue supporting means includes a knife anvil against which the knife means cuts the tissue.

23. The apparatus defined in claim 22 wherein the means responsive to motion of the actuator includes means for causing the knife means to move toward the tissue supporting means as the tissue supporting means is moving away from the clip applying assembly so that the knife means contacts the knife anvil and thereby cuts the tissue.

24. The apparatus defined in claim 23 wherein the means responsive to motion of the actuator includes means for allowing the knife means to force the tissue supporting means away from the clip applying assemblies after the knife means has contacted the knife anvil.

25. The method of ligating and dividing an organic tissue structure comprising the steps of:

positioning a tissue supporting structure on one side of the tissue structure to be ligated;

moving a clip applying assembly toward the tissue supporting structure so that the tissue is introduced into the jaws of each of two laterally spaced clip closing structures, the jaws of each structure being spaced apart and rigidly fixed relative to one another;

operating the clip applying assembly to force two laterally spaced clips through the jaws to close the clips on the tissue and to subsequently eject the closed clips from the jaws;

moving the tissue supporting structure away from the clip applying assembly while the closed clips are being ejected from the jaws so that the tissue supporting assembly does not impede ejection of the clips from the jaws; and cutting the tissue between the closed clips during ejection of the clips from the jaws.

* * * * *